United States Patent
Kraatz et al.

(10) Patent No.: US 7,250,521 B2
(45) Date of Patent: Jul. 31, 2007

(54) METHOD FOR PRODUCTION OF $\Delta^1$-PYRROLINES

(75) Inventors: Udo Kraatz, Leverkusen (DE); Andrew Plant, Berkshire (GB); Ernst Kysela, Bergisch Gladbach (DE); Albrecht Marhold, Leverkusen (DE)

(73) Assignee: Bayer CropScience Aktiengesellschaft

( * ) Notice: Subject to any disclaimer, the term of this patent is extended or adjusted under 35 U.S.C. 154(b) by 272 days.

(21) Appl. No.: 10/474,106

(22) PCT Filed: Apr. 8, 2002

(86) PCT No.: PCT/EP02/03855

§ 371 (c)(1),
(2), (4) Date: Mar. 8, 2004

(87) PCT Pub. No.: WO02/081442

PCT Pub. Date: Oct. 17, 2002

(65) Prior Publication Data
US 2004/0147764 A1     Jul. 29, 2004

(30) Foreign Application Priority Data

Apr. 9, 2001 (DE) ................ 101 17 675
Jul. 12, 2001 (DE) ................ 101 33 929

(51) Int. Cl.
*C07D 207/18* (2006.01)
(52) U.S. Cl. ...................... 548/565; 548/566
(58) Field of Classification Search ................ 548/525, 548/527, 565, 566
See application file for complete search history.

(56) References Cited

U.S. PATENT DOCUMENTS

| | | | | |
|---|---|---|---|---|
| 6,274,613 B1 | 8/2001 | Plant et al. | ................ | 514/408 |
| 6,399,771 B1 | 6/2002 | Plant et al. | ................ | 540/611 |
| 6,489,490 B1 * | 12/2002 | Plant et al. | ................ | 548/525 |
| 6,599,924 B1 | 7/2003 | Plant et al. | ................ | 514/343 |
| 6,632,833 B1 * | 10/2003 | Plant et al. | ................ | 514/422 |
| 2002/0151571 A1 | 10/2002 | Plant et al. | ................ | 514/357 |

FOREIGN PATENT DOCUMENTS

| | | | |
|---|---|---|---|
| CA | 2332522 | | 11/1999 |
| WO | WO/ 98/22438 | * | 5/1998 |
| WO | 99/59968 | | 11/1999 |
| WO | WO/ 99/59967 | * | 11/1999 |
| WO | 00/50380 | | 8/2000 |

OTHER PUBLICATIONS

Profft et al., 1956, CAS:50:4732.*
Koller et al., 1963, CAS: 58:59652.*
J. Org. Chem., 63, (month unavailable) 1998, pp. 1109-1118, Leo S. Bleicher et al, "A Practical and Efficient Synthesis of the Selective Neuronal Acetylcholine-Gated Ion Channel Agonist (*S*)-(− )-5-Ethynyl-3-(1-methyl-2-pyrrolidinyl)pyridine Maleate (SIB-1508Y)".
J. Org. Chem., 47, (month unavailable) 1982, pp. 4165-4167, Peyton Jacob III, "Resolution of (±)-5-Bromonornicotine. Synthesis of (*R*)- and (*S*)-Nornicotine of High Enantiomeric Purity".
Org. Prep. Proced. Int. 27, (month unavailable) 1995, pp. 510-513, John A. Zoltewicz et al, "A Superior Synthesis of Cholinergic Anabaseine".
Tetrahedron Letters, 39, (month unavailable) 1998, pp. 2705-2706, Marvin M. Hansen et al "A Novel Protecting Group for Hindered Phenols".
J. Prakt. Chem., 342, (month unavailable) 2000, pp. 340-347, Jaimala Singh et al, "The Growing Synthetic Utility of Weinreb's Amide".
Org. Prep. Proced. Int., 27, (month unavailable) 1993, pp. 255-258, Z.Y. Wei et al, "A Practical Procedure for the Synthesis of 5-Substituted γ-Lactams".
Org. Prep. Proced. Int., 27, (month unavailable) 1995, pp. 550-552, Rafael Castillo et al, "An Improved Synthesis of Fenbufen".
Syn. Commun., 26, (month unavailable) 1996, pp. 3897-3901, G. Lhommet et al, "A General and Versatile Synthesis of 4- and 5-Oxoacids".

(Continued)

*Primary Examiner*—Kamal A. Saeed
*Assistant Examiner*—Rei-tsang Shiao
(74) *Attorney, Agent, or Firm*—Raymond J. Harmuth

(57) ABSTRACT

2,5-Bisaryl-$\Delta^1$-pyrrolines of the formula (I)

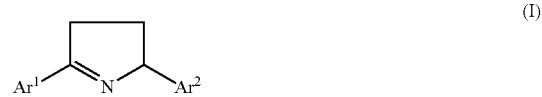

(I)

in which
$Ar^1$ and $Ar^2$ are as defined in the description
can be prepared by
reacting aroylpyrrolidinones of the formula (II)

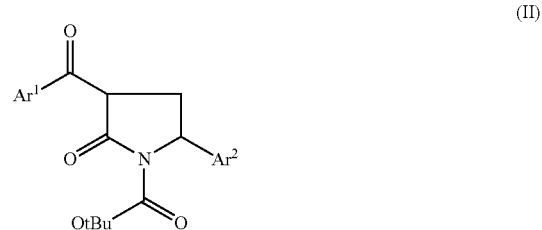

(II)

in which
$Ar^1$ and $Ar^2$ are as defined in the description
with an acid, if appropriate in the presence of a diluent.

19 Claims, No Drawings

OTHER PUBLICATIONS

Chem. Pharm. Bull., 36, (month unavailable) 1988, pp. 2050-2060, Kazuya Kameo et al, "Studies on Antirheumatic Agents: 3-Benzoylpropionic Acid Derivatives".

Tetrahedron, 31, (month unavailable) 1975, pp. 1437-1441, J.C. Hubert et al, "NaBH$_4$ Reduction of Cyclic Imides".

Heterocycles, 20, (month unavailable) 1983, pp. 985-990, Tatsuo Nagasaka et al, "5-Acetoxy-2-Pyrrolidinone as a Precursor for N-Acylimminium Ion".

J. Med. Chem., 39, (month unavailable) 1996, pp. 4396-4405, Luca Costantino et al, "Synthesis, Activity, and Molecular Modeling of a New Series of Tricyclic Pyridazinones as Selective Aldose Reductase Inhibitors".

Haslego M L et al: "A Practical Preparation of Deltai-2-Substituted and Delta1-2,3-Disubstituted Pyrrolines" Heterocycles, Elsevier Science Publishers B.V. Amsterdam, NL, Bd. 35, Nr. 2, May 1, 1993, Seiten 643-647, XP002045516.

* cited by examiner

METHOD FOR PRODUCTION OF Δ¹-PYRROLINES

The present invention relates to a novel process for preparing 2,5-bisaryl-Δ¹-pyrrolines.

Δ¹-Pyrrolines, processes for their preparation and their use as pesticides are already described in WO 00/21958, WO 99/59968, WO 99/59967 and WO 98/22438. However, in terms of yield, practice of the reaction, the number of byproducts, the kind of work-up, the amount of waste produced and the energy requirements, these processes are unsatisfactory. Accordingly, there is a constant need for novel processes which overcome one or more of the disadvantages mentioned.

It has now been found that 2,5-bisaryl-Δ¹-pyrrolines of the formula (I)

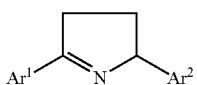

(I)

in which
$Ar^1$ represents the radical

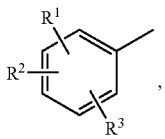

$Ar^2$ represents the radical

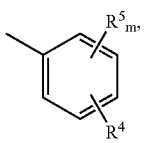

m represents 1, 2, 3 or 4,
$R^1$ represents halogen, cyano, nitro, alkyl, alkoxy, haloalkyl, haloalkoxy, alkoxyalkyl or $—S(O)_oR^6$,
$R^2$ and $R^3$ independently of one another represent hydrogen, halogen, cyano, nitro, alkyl, alkoxy, haloalkyl, haloalkoxy, alkoxyalkyl or $—S(O)_oR^6$,
$R^4$ represents halogen or one of the groupings below
  (l) —X—A
  (m) —B—Z—D
  (n) —Y—E
$R^5$ represents hydrogen, halogen, hydroxyl, cyano, alkyl, alkylcarbonyl, alkoxy, haloalkyl, haloalkoxy, trialkylsilyl, alkoxycarbonyl, $—CONR^7R^8$, $—OSO_2NR^7R^8$ or $—S(O)_o R^6$,
X represents a direct bond, O (oxygen), $S(O)_o$, $NR^6$, carbonyl, carbonyloxy, oxycarbonyl, oxysulfonyl ($OSO_2$), alkylene, alkenylene, alkynylene, alkylen-oxy, oxyalkylene, oxyalkylenoxy, thioalkylene, cyclopropylene or oxiranylene,
A represents phenyl, naphthyl or tetrahydronaphthyl, each of which is optionally mono- or polysubstituted by radicals from the list $W^1$, or represents 5- to 10-membered saturated or unsaturated heterocyclyl which contains one or more heteroatoms from a group consisting of nitrogen, oxygen and sulfur and which is in each case optionally mono- or polysubstituted by radicals from the list $W^2$,
B represents p-phenylene which is optionally mono- or disubstituted by radicals from the list $W^1$,
Z represents $(CH_2)_n$, O (oxygen) or $S(O)_o$,
D represents hydrogen, alkyl, alkenyl, alkynyl, haloalkyl, haloalkenyl, alkoxycarbonyl, haloalkylsulfonyl or dialkylamninosulfonyl,
Y represents a direct bond, O (oxygen), S (sulfur), $SO_2$, carbonyl, carbonyloxy, oxycarbonyl, alkylene, alkenylene, alkynylene, haloalkylene, haloalkenylene, alkylenoxy, oxyalkylene, oxyalkylenoxy or thioalkylene,
E represents hydrogen, alkyl, alkenyl, alkynyl, haloalkyl, haloalkenyl, haloalkylsulfonyl, cycloalkyl, dialkylaminocarbonyl or dialkylaminosulfonyl,
$W^1$ represents cyano, halogen, formyl, nitro, alkyl, trialkylsilyl, alkoxy, haloalkyl, haloalkoxy, haloalkenyloxy, haloalkylsulfonyloxy, alkylcarbonyl, alkoxycarbonyl, $—S(O)_oR^6$, $—SO_2NR^7R^8$, or $—OSO_2NR^7R^8$,
$W^2$ represents cyano, halogen, formyl, nitro, alkyl, trialkylsilyl, alkoxy, haloalkyl, haloalkoxy, haloalkenyloxy, haloalkenylsulfonyloxy, alkylcarbonyl, alkoxycarbonyl, $—S(O)_oR^6$, $—SO_2NR^7R^8$, $—OSO_2NR^7R^8$ or $—NR^7R^8$,
n represents 0, 1, 2, 3 or 4,
o represents 0, 1 or 2,
$R^6$ represents hydrogen, alkyl or haloalkyl,
$R^7$ and $R^8$ independently of one another represent hydrogen, alkyl, haloalkyl, or together represent alkylene, alkoxyalkylene or alkylthioalkylene, where the compounds of the formula (I) may, depending on the nature and the number of substituents, be present as geometrical and/or optical isomers, regioisomers or configurational isomers or isomer mixtures thereof of varying composition, can be prepared by reacting aroylpyrrolidinones of the formula (II)

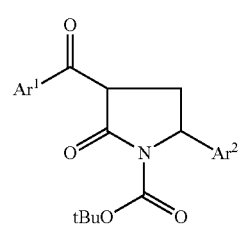

(II)

in which
$Ar^1$ and $Ar^2$ are as defined above with an acid, if appropriate in the presence of a diluent.

It is extremely surprising that 2,5-bisaryl-Δ¹-pyrrolines of the formula (I) can be prepared by the process according to the invention in a smooth reaction without interfering side reactions, in high yields and with high purity.

The process according to the invention is characterized by the following further advantage. Owing to the course of the reaction, the pyrrolines formed are obtained as only one double bond isomer with respect to the double bond in the pyrroline ring. The double bond in the ring is always located between the nitrogen atom and the carbon atom to which $Ar^1$ is attached. A possible shift of the C=C double bond has not been observed under the conditions of the process according to the invention.

Using tert-butyl 3-(2-bromobenzoyl)-2-oxo-5-[4-(trifluoromethoxy)phenyl]-1-pyrrolidinecarboxylate as starting material and sulfuric acid, the course of the process according to the invention can be illustrated by the formula scheme below.

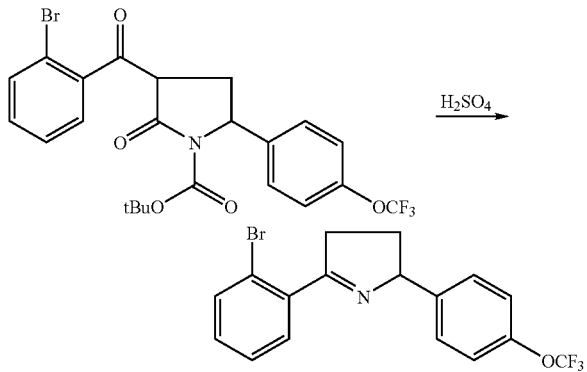

The formula (II) provides a general definition of the amides required as starting materials for carrying out the process according to the invention.

Preferred substituents or ranges in the formulae of starting materials of the formula (II) shown above and below are illustrated below.

$Ar^1$ preferably represents the radical

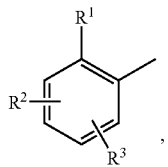

$Ar^2$ preferably represents the radical

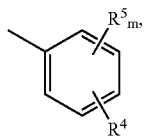

m preferably represents 1, 2 or 3.

$R^1$ preferably represents halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkoxyalkyl or —S(O)$_o$R$^6$.

$R^2$ and $R^3$ independently of one another preferably represent hydrogen, halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkoxy-$C_1$-$C_6$-alkyl or —S(O)$_o$R$^6$.

$R^4$ preferably represents fluorine, chlorine, bromine, iodine or one of the groupings below.
(l) —X—A
(m) —B—Z—D
(n) —Y—E $R^5$ preferably represents hydrogen, halogen, hydroxyl, cyano, $C_1$-$C_6$-alkyl, $C_1$-$C_6$-alkylcarbonyl, $C_1$-$C_6$-alkoxy, $C_1$-$C_6$-haloalkyl, $C_1$-$C_6$-haloalkoxy, tri($C_1$-$C_6$-alkyl)silyl, $C_1$-$C_6$-alkoxycarbonyl, —CONR$^7$R$^8$, —OSO$_2$NR$^7$R$^8$ or —S(O)$_o$R$^6$.

X preferably represents a direct bond, O (oxygen), S(O)$_o$, NR$^6$, carbonyl, carbonyloxy, oxycarbonyl, oxysulfonyl (OSO$_2$), $C_1$-$C_4$-alkylene, $C_2$-$C_4$-alkenylene, $C_2$-$C_4$-alkynylene, $C_1$-$C_4$-alkylenoxy, $C_1$-$C_4$-oxyalkylene, $C_1$-$C_4$-oxyalkylenoxy, thio-$C_1$-$C_4$-alkylene, cyclopropylene or oxiranylene.

A preferably represents phenyl, naphthyl or tetrahydronaphthyl, each of which is optionally mono- to tetrasubstituted by radicals from the list W$^1$, or represents 5- to 10-membered heterocyclyl which contains 1 or 2 aromatic rings and 1 to 4 heteroatoms, as a combination of 0 to 4 nitrogen atoms, 0 to 2 oxygen atoms and/or 0 to 2 sulfur atoms (in particular tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl, triazyl, quinolinyl or isoquinolinyl) and which is in each case optionally mono- to tetrasubstituted by radicals from the list W$^2$.

B preferably represents p-phenylene which is optionally mono- or disubstituted by radicals from the list W$^1$.

Z preferably represents (CH$_2$)$_n$, O (oxygen) or S(O)$_o$.

D preferably represents hydrogen, $C_1$-$C_6$-alkyl, $C_1$-$C_6$-alkenyl, $C_2$-$C_6$-alkynyl, $C_1$-$C_6$-haloalkyl, $C_2$-$C_6$-haloalkenyl, $C_1$-$C_6$-alkoxycarbonyl, $C_1$-$C_6$-halo-alkylsulfonyl or di($C_1$-$C_6$-alkyl)aminosulfonyl.

Y preferably represents a direct bond, O (oxygen), S (sulfur), SO$_2$, carbonyl, carbonyloxy, oxycarbonyl, $C_1$-$C_6$-alkylene, $C_2$-$C_6$-alkenylene, $C_2$-$C_6$-alkynylene, $C_1$-$C_6$-haloalkylene, $C_2$-$C_6$-haloalkenylene, $C_1$-$C_4$-alkylenoxy, $C_1$-$C_4$-oxyalkylene, $C_1$-$C_4$-oxyalkylenoxy or thio-$C_1$-$C_4$-alkylene.

E preferably represents hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-haloalkylsulfonyl, $C_3$-$C_7$-cycloalkyl, di($C_1$-$C_6$-alkyl)aminocarbonyl or di($C_1$-$C_6$-alkyl)aminosulfonyl.

W$^1$ preferably represents cyano, halogen, formyl, nitro, $C_1$-$C_6$-alkyl, $C_1$-$C_4$-tri-alkylsilyl, $C_1$-$C_6$-alkoxy, $C_1$-$C_6$-haloalkyl, $C_1$-$C_6$-haloalkoxy, $C_2$-$C_6$-halo-alkenyloxy, $C_1$-$C_6$-haloalkylsulfonyloxy, $C_1$-$C_6$-alkylcarbonyl, $C_1$-$C_6$-alkoxycarbonyl, —S(O)$_o$R$^6$, —SO$_2$NR$^7$R$^8$ or —OSO$_2$NR$^7$R$^8$.

W$^2$ preferably represents cyano, halogen, formyl, nitro, $C_1$-$C_6$-alkyl, tri($C_1$-$C_4$-alkyl)silyl, $C_1$-$C_6$-alkoxy, $C_1$-$C_6$-haloalkyl, $C_1$-$C_6$-haloalkoxy, $C_2$-$C_6$-haloalkenyloxy, $C_1$-$C_6$-haloalkylsulfonyloxy, $C_1$-$C_6$-alkylcarbonyl, $C_1$-$C_6$-alkoxycarbonyl, —S(O)$_o$R$^6$, —SO$_2$NR$^7$R$^8$, —OSO$_2$NR$^7$R$^8$ or —NR$^7$R$^8$.

n preferably represents 0, 1, 2, 3 or 4.

o preferably represents 0, 1 or 2.

R$^6$ preferably represents hydrogen, $C_1$-$C_6$-alkyl or $C_1$-$C_6$-haloalkyl.

R$^7$ and R$^8$ independently of one another preferably represent hydrogen, $C_1$-$C_6$-alkyl, $C_1$-$C_6$-haloalkyl, or together represent $C_2$-$C_6$-alkylene, $C_1$-$C_4$-alkoxy-$C_1$-$C_4$-alkyl (for example morpholine) or $C_1$-$C_4$-alkylthio-$C_1$-$C_4$-alkyl (for example thiomorpholine).

Ar¹ particularly preferably represents the radical

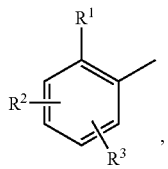

Ar² particularly preferably represents the radical

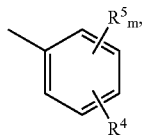

m particularly preferably represents 1 or 2.

R¹ particularly preferably represents fluorine, chlorine, bromine, $C_1$-$C_6$-alkyl, $C_1$-$C_6$-alkoxy, $C_1$-$C_6$-haloalkyl having 1 to 13 fluorine and/or chlorine atoms or $C_1$-$C_6$-haloalkoxy having 1 to 13 fluorine and/or chlorine atoms.

R² and R³ independently of one another particularly preferably represent hydrogen, fluorine, chlorine, bromine, $C_1$-$C_6$-alkyl, $C_1$-$C_6$-alkoxy, $C_1$-$C_6$-haloalkyl having 1 to 13 fluorine and/or chlorine atoms or $C_1$-$C_6$-haloalkoxy having 1 to 13 fluorine and/or chlorine atoms, R⁴ particularly preferably represents fluorine, chlorine, bromine, iodine or one of the groupings below
(l) —X—A
(m) —B—Z—D
(n) —Y—E R⁵ particularly preferably represents hydrogen, fluorine, chlorine, bromine, hydroxyl, cyano, $C_1$-$C_6$-alkyl, $C_1$-$C_6$-alkylcarbonyl, $C_1$-$C_6$-alkoxy, $C_1$-$C_6$-haloalkyl having 1 to 13 fluorine and/or chlorine atoms, $C_1$-$C_6$-haloalkoxy having 1 to 13 fluorine and/or chlorine atoms or —S(O)$_o$R⁶.

X particularly preferably represents a direct bond, O (oxygen), S (sulfur), SO₂, carbonyl, carbonyloxy, oxycarbonyl, oxysulfonyl (OSO₂), $C_1$-$C_4$-alkylene, $C_2$-$C_4$-alkenylene, $C_2$-$C_4$-alkynylene, $C_1$-$C_4$-alkylenoxy, $C_1$-$C_4$-oxyalkylene, $C_1$-$C_4$-oxyalkylenoxy, thio-$C_1$-$C_4$-alkylene, cyclopropylene or oxiranylene.

A particularly preferably represents phenyl, naphthyl or tetrahydronaphthyl, each of which is optionally mono- to trisubstituted by radicals from the list W¹, or represents 5- to 10-membered heterocyclyl which contains 1 or 2 aromatic rings and 1 to 4 heteroatoms, as a combination of 0 to 4 nitrogen atoms, 0 to 2 oxygen atoms and/or 0 to 2 sulfur atoms (in particular tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl, triazyl, quinolinyl or isoquinolinyl) and which is in each case optionally mono- to trisubstituted by radicals from the list W².

B particularly preferably represents p-phenylene which is optionally mono- or disubstituted by radicals from the list W¹.

Z particularly preferably represents (CH₂)$_n$, O (oxygen) or S(O)$_o$.

D particularly preferably represents hydrogen, $C_1$-$C_6$-alkyl, $C_1$-$C_6$-alkenyl, $C_2$-$C_6$-alkynyl, $C_1$-$C_6$-haloalkyl having 1 to 13 fluorine and/or chlorine atoms, $C_2$-$C_6$-haloalkenyl having 1 to 11 fluorine and/or chlorine atoms, $C_1$-$C_6$-alkoxycarbonyl, $C_1$-$C_6$-haloalkylsulfonyl having 1 to 13 fluorine and/or chlorine atoms or di($C_1$-$C_4$-alkyl)aminosulfonyl.

Y particularly preferably represents a direct bond, O (oxygen), S (sulfur), SO₂, carbonyl, carbonyloxy, oxycarbonyl, $C_1$-$C_6$-alkylene, $C_2$-$C_6$-alkenylene, $C_2$-$C_6$-alkynylene, $C_1$-$C_6$-haloalkylene having 1 to 12 fluorine and/or chlorine atoms, $C_2$-$C_6$-haloalkenylene having 1 to 10 fluorine and/or chlorine atoms, $C_1$-$C_4$-alkylenoxy, $C_1$-$C_4$-oxyalkylene, $C_1$-$C_4$-oxyalkylenoxy or thio-$C_1$-$C_4$-alkylene.

E particularly preferably represents hydrogen, $C_1$-$C_6$-alkyl, $C_2$-$C_6$-alkenyl, $C_2$-$C_6$-alkynyl, $C_1$-$C_6$-haloalkyl having 1 to 13 fluorine and/or chlorine atoms, $C_2$-$C_6$-haloalkenyl having 1 to 11 fluorine and/or chlorine atoms, $C_1$-$C_6$-haloalkylsulfonyl having 1 to 13 fluorine and/or chlorine atoms, $C_3$-$C_6$-cycloalkyl, di($C_1$-$C_6$-alkyl)aminocarbonyl or di($C_1$-$C_6$-alkyl)aminosulfonyl.

W¹ particularly preferably represents fluorine, chlorine, bromine, $C_1$-$C_4$-alkyl, $C_1$-$C_4$-alkoxy, $C_1$-$C_4$-haloalkyl having 1 to 9 fluorine and/or chlorine atoms, $C_1$-$C_4$-haloalkoxy having 1 to 9 fluorine and/or chlorine atoms, $C_1$-$C_4$-alkylcarbonyl, $C_1$-$C_4$-alkoxycarbonyl, —SO₂NR⁷R⁸ or —S(O)$_o$R⁶.

W² particularly preferably represents fluorine, chlorine, bromine, $C_1$-$C_4$-alkyl, $C_1$-$C_4$-alkoxy, $C_1$-$C_4$-haloalkyl having 1 to 9 fluorine and/or chlorine atoms, $C_1$-$C_4$-haloalkoxy having 1 to 9 fluorine and/or chlorine atoms, $C_2$-$C_6$-haloalkenyloxy having 1 to 11 fluorine and/or chlorine atoms, $C_1$-$C_4$-alkylcarbonyl, $C_1$-$C_4$-alkoxycarbonyl, —SO₂NR⁷R⁸ or —S(O)$_o$R⁶.

n particularly preferably represents 0, 1, 2 or 3.

o particularly preferably represents 0, 1 or 2.

R⁶ particularly preferably represents $C_1$-$C_6$-alkyl or represents methyl or ethyl, each of which is substituted by 1 to 5 fluorine and/or chlorine atoms.

R⁷ and R⁸ independently of one another particularly preferably represent hydrogen, $C_1$-$C_4$-alkyl, $C_1$-$C_4$-haloalkyl having 1 to 9 fluorine, chlorine and/or bromine atoms, or together represent —(CH₂)₅—, —(CH₂)₄—, —(CH₂)₂—O—(CH₂)₂— or —(CH₂)₂—S—(CH₂)₂—.

Ar¹ very particularly preferably represents the radical

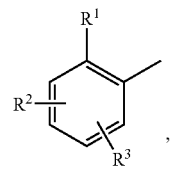

Ar² very particularly preferably represents the radical

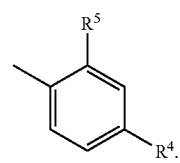

R¹ very particularly preferably represents fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, trifluoromethyl or trifluoromethoxy.

$R^2$ and $R^3$ independently of one another very particularly preferably represent hydrogen, fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, trifluoromethyl or trifluoromethoxy.

$R^4$ very particularly preferably represents fluorine, chlorine, bromine or one of the groupings below
(l) —X—A
(m) —B—Z—D
(n) —Y—E $R^5$ very particularly preferably represents hydrogen, fluorine, chlorine, bromine, hydroxyl, methyl, ethyl, methoxy, ethoxy, i-propoxy, methylthio, ethylthio, trifluoromethyl, difluoromethoxy, trifluoromethoxy, trifluoromethylthio or —SO$_2$CF$_3$.

X very particularly preferably represents a direct bond, O (oxygen), S (sulfur), SO$_2$, carbonyl, —CH$_2$—, —(CH$_2$)$_2$—, —CH═CH— (E or Z), —C≡C—, —CH$_2$O—, —(CH$_2$)$_2$O—, —OCH$_2$—, —SCH$_2$—, —S(CH$_2$)$_2$—, —OCH$_2$O— or —O(CH$_2$)$_2$O—.

A very particularly preferably represents phenyl which is optionally mono- or disubstituted by radicals from the list W$^1$ or represents tetrazolyl, furyl, benzofuryl, thienyl, benzothienyl, pyrrolyl, indolyl, oxazolyl, benzoxazolyl, isoxazyl, imidazyl, pyrazyl, thiazolyl, benzothiazolyl, pyridyl, pyrimidinyl, pyridazyl, triazinyl or triazyl, each of which is optionally mono- or disubstituted by radicals from the list W$^2$.

B very particularly preferably represents p-phenylene which is optionally monosubstituted by radicals from the list W$^1$.

Z very particularly preferably represents O (oxygen), S (sulfur) or SO$_2$.

D very particularly preferably represents hydrogen, methyl, ethyl, n-propyl, i-propyl, n-butyl, i-butyl, s-butyl, t-butyl, 2-propenyl, butenyl, propargyl, butynyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —CO$_2$Me, —CO$_2$Et, —SO$_2$CF$_3$, —SO$_2$(CF$_2$)$_3$CF$_3$, —SO$_2$NMe$_2$.

Y very particularly preferably represents a direct bond, O (oxygen), S (sulfur), SO$_2$, carbonyl, —CH$_2$—, —(CH$_2$)$_2$—, —CH═CH— (E or Z), —C≡C—, —CH$_2$O—, —(CH$_2$)$_2$O—, —OCH$_2$—, —SCH$_2$—, —S(CH$_2$)$_2$—, —OCH$_2$O— or —O(CH$_2$)$_2$O—.

E very particularly preferably represents hydrogen, methyl, ethyl, n-propyl, i-propyl, n-butyl, i-butyl, s-butyl, t-butyl, 2-propen-1-yl, butenyl, propargyl, butynyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —SO$_2$CF$_3$, —SO$_2$(CF$_2$)$_3$CF$_3$, cyclohexyl, dimethylaminocarbonyl, —SO$_2$NMe$_2$.

W$^1$ very particularly preferably represents fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, trifluoromethoxy, difluoromethoxy, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, CF$_2$CF$_2$H, —CF$_2$CHFCF$_3$, —SCF$_3$, —SCHF$_2$, —SO$_2$CHF$_2$, —SO$_2$CF$_3$, —SO$_2$NMe$_2$, —COCH$_3$ or —SO$_2$Me$_2$.

W$^2$ very particularly preferably represents fluorine, chlorine, bromine, methyl, ethyl, n-propyl, i-propyl, t-butyl, trifluoromethyl, trifluoromethoxy, difluoromethoxy, trifluoromethylthio, —COCH$_3$, —SO$_2$CF$_3$ or —SO$_2$NMe$_2$.

Particularly preferred starting materials for the process according to the invention are the compounds of the formula (II-a)

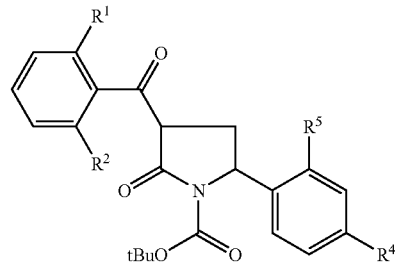

(II-a)

in which $R^1$ represents halogen, methyl, methoxy, trifluoromethyl or trifluoromethoxy, $R^2$ represents hydrogen or halogen, $R^4$ represents phenyl which is mono- or disubstituted by radicals from the list W$^1$ or represents heterocyclyl which is mono- or disubstituted from the list W$^2$ or represents the grouping —Y—E, $R^5$ represents hydrogen or alkoxy and Y, E, W$^1$ and W$^2$ have the meanings given above as general, preferred, particularly preferred and/or very particularly preferred.

Very particular preference is given to starting materials of the formula (II-a) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from the list W$^1$ or represents heterocyclyl which is mono- or disubstituted from the list W$^2$ or represents the grouping —Y—E, $R^5$ represents hydrogen or C$_1$-C$_6$-alkoxy and Y, E, W$^1$ and W$^2$ have the meanings given above as general, preferred, particularly preferred and/or very particularly preferred.

Especially preferred are starting materials of the formula (II-a) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from the list W$^1$ or represents heterocyclyl which is mono- or disubstituted from the list W$^2$ or represents the grouping —Y—E, $R^5$ represents hydrogen, methoxy or ethoxy and Y, E, W$^1$ and W$^2$ have the meanings given above as general, preferred, particularly preferred and/or very particularly preferred.

Starting materials for the process according to the invention which are likewise emphasized are the compounds of the formula (II-b)

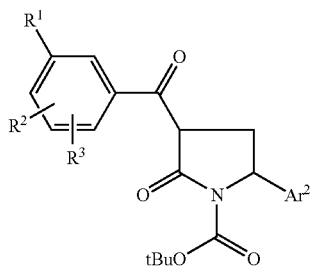

(II-b)

in which

Ar², R¹, R² and R³ are as defined above.

Starting materials for the process according to the invention which are likewise emphasized are the compounds of the formula (II-c)

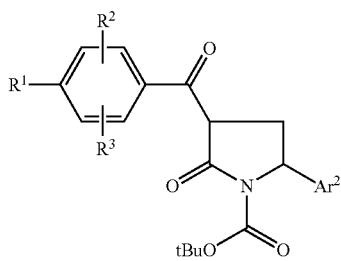

(II-c)

in which

Ar², R¹, R² and R³ are as defined above.

Preference is given to compounds of the formulae (II-b) and (II-c), in which Ar², R¹, R² and R³ have the meanings given above as being preferred for these radicals.

Particular preference is given to compounds of the formulae (II-b) and (II-c) in which Ar², R¹, R² and R³ have the meanings given above as being particularly preferred for these radicals.

Very particular preference is given to the compounds of the formulae (II-b) and (II-c) in which Ar², R¹, R² and R³ have the meanings given above as being very particularly preferred for these radicals.

Starting materials for the process according to the invention which are likewise emphasized are the compounds of the formula (II-d)

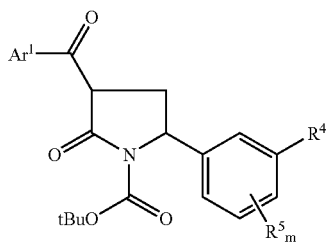

(II-d)

in which

Ar¹, R⁴, R⁵ and m are as defined above.

Starting materials for the process according to the invention which are likewise emphasized are the compounds of the formula (II-e)

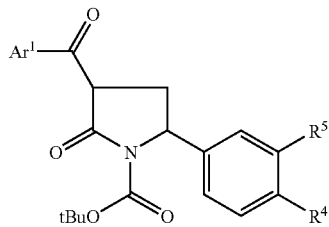

(II-e)

in which

Ar¹, R⁴, R⁵ and m are as defined above.

Preference is given to compounds of the formulae (II-d) and (II-e), in which R¹, R², R³ and Ar² have the meanings given above as being preferred for these radicals.

Particular preference is given to the compounds of the formulae (II-d) and (II-e), in which R¹, R², R³ and Ar² have the meanings given above as being particularly preferred for these radicals.

Very particular preference is given to the compounds of the formulae (II-d) and (II-e) in which R¹, R², R³ and Ar² have the meanings given above as being very particularly preferred for these radicals.

Particularly preferred starting materials for the process according to the invention are the compounds of the formula (II-f)

(II-f)

in which $R^1$ represents halogen, methyl, methoxy, trifluoromethyl or trifluoromethoxy, $R^2$ represents hydrogen or halogen, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or alkoxy and Y, E, $W^1$ and $W^2$ have the general, preferred, particularly preferred and/or very particularly preferred meanings given above.

Very particular preference is given to starting materials of the formula (II-f) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or $C_1$-$C_6$-alkoxy and Y, E, $W^1$ and $W^2$ have the general, preferred, particularly preferred and/or very particularly preferred meanings given above.

Especially preferred are starting materials of the formula (II-f) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen, methoxy or ethoxy and Y, E, $W^1$ and $W^2$ have the general, preferred, particularly preferred and/or very particularly preferred meanings given above.

Particularly preferred starting materials for the process according to the invention are the compounds of the formula (II-g)

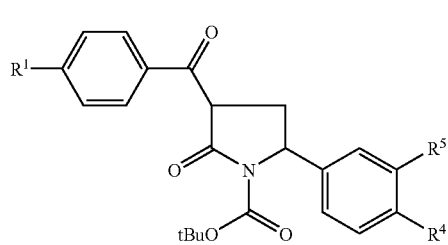

in which $R^1$ represents halogen, methyl, methoxy, trifluoromethyl or trifluoromethoxy, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or alkoxy and Y, E, $W^1$ and $W^2$ have the general, preferred, particularly preferred and/or very particularly preferred meanings given above.

Very particular preference is given to starting materials of the formula (II-g) in which $R^1$ represents fluorine, chlorine, methyl, methoxy, trifluoromethyl or trifluoromethoxy, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or $C_1$-$C_6$-alkoxy and Y, E, $W^1$ and $W^2$ have the general, preferred, particularly preferred and/or very particularly preferred meanings given above.

Especially preferred are starting materials of the formula (II-g) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen, methoxy or ethoxy and Y, E, $W^1$ and $W^2$ have the general, preferred, particularly preferred and/or very particularly preferred meanings given above.

In the definitions mentioned above, oxyalkylene and thioalkylene represent —O-alkyl- and —S-alkyl-, respectively, where the bond for example to $Ar^2$ is via the oxygen and sulfur atom, respectively, and further substituents may be attached to the alkyl radical, such as, for example, A in —X—A. Alkylenoxy and alkylenethio represent -alkyl-O— and -alkyl-S—, respectively, where the bond for example to $Ar^2$ is in each case via the alkyl radical and further substituents may be attached to the oxygen and sulfur atom, respectively, such as, for example, A in —X—A. Oxyalkylenoxy represents —O-alkyl-O—.

In the present description, heterocyclyl denotes a cyclic hydrocarbon in which one or more carbons are replaced by one or more heteroatoms. Preferred heteroatoms are O, S, N, P, in particular O, S and N.

Preferred, particularly preferred or very particularly preferred are compounds which carry the substituents mentioned under preferred, particularly preferred or very particularly preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different. The plurality of radicals having the same indices, such as, for example, m radicals $R^5$ for m >1, can be identical or different.

Halogen-substituted radicals, such as, for example, haloalkyl, are mono- or polyhalogenated. In the case of polyhalogenation, the halogen atoms can be identical or different. Halogen denotes fluorine, chlorine, bromine or iodine, in particular fluorine or chlorine.

However, the abovementioned general or preferred radical definitions or illustrations can also be combined with one another as desired, i.e. including combinations between the respective ranges and preferred ranges. They apply both to the end products and, correspondingly, to precursors and intermediates.

The aroylpyrrolidinones of the formula (II) required as starting materials for carrying out the process according to the invention are novel. They can be prepared by a) reacting lactams of the formula (III)

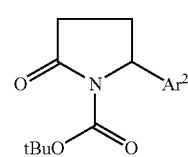

in which $Ar^2$ is as defined above with a compound of the formula (IV)

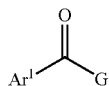

in which

Ar¹ is as defined above and

G represents chlorine, $C_1$-$C_6$-alkoxycarbonyl or —N(OCH$_3$)CH$_3$, in the presence of a base [for example lithium bis(trimethylsilyl)amide] and in the presence of a diluent (for example tetrahydrofuran) (cf. J. Org. Chem. 1998, 63, 1109; J. Org Chem. 1982, 47, 4165; Org. Prep. Proced. Int. 1995, 27, 510).

The formula (III) provides a general definition of the lactams required as starting materials for carrying out the process (a) according to the invention. In this formula, Ar² preferably, particularly preferably or very particularly preferably has those meanings which have already been mentioned in connection with the description of the starting materials of the formula (II) as being preferred, particularly preferred, etc., for these radicals.

Lactams of the formula (III) are known. They can be prepared, for example, by b) reacting pyrrolidinones of the formula (V)

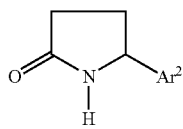

in which

Ar² is as defined above with di-tert-butyl dicarbonate in the presence of a base (for example dimethyl-aminopyridine) and, if appropriate, in the presence of a diluent (for example dimethylformamide) (cf. Tetrahedron Letters, 1998, 39, 2705-2706).

The formula (IV) provides a general definition of the compounds required as starting materials for carrying out the process (a) according to the invention. In this formula, Ar¹ preferably, particularly preferably or very particularly preferably has those meanings which have already been mentioned in connection with the description of the starting materials of the formula (II) as being preferred, particularly preferred, etc., for these radicals. G preferably represents chlorine, methoxycarbonyl, ethoxycarbonyl, i-propoxycarbonyl, t-butoxycarbonyl or —N(OCH$_3$)CH$_3$.

Compounds of the formula (IV) are known and/or can be prepared by known processes (cf. J. Prakt. Chem. 2000, 342, 340).

The formula (V) provides a general definition of the pyrrolidinones required as starting materials for carrying out the process (b) according to the invention. In this formula, Ar² preferably, particularly preferably or very particularly preferably has those meanings which have already been mentioned in connection with the description of the starting materials of the formula (II) as being preferred, particularly preferred, etc., for these radicals.

Pyrrolidinones of the formula (V) are known. They can be prepared, for example, by c) reacting ketocarboxylic acids of the formula (VI)

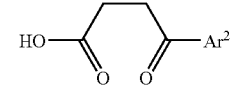

in which

Ar² is as defined above with ammonia and hydrogen in the presence of a catalyst (for example Raney nickel) and, if appropriate, in the presence of a diluent (for example ethanol) under pressure or d) reacting hemi-aminals of the formula (VII)

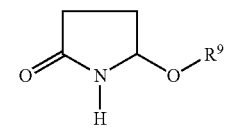

in which

R⁹ represents alkyl or alkylcarbonyl with aromatic compounds of the formula (VIII)

H—Ar² (VIII)

in which

Ar² is as defined above with a protic acid (for example hydrofluoric acid) or with a Lewis acid and, if appropriate, in the presence of a diluent (for example dichloromethane)

or e) reacting hemi-aminals of the formula (VII)

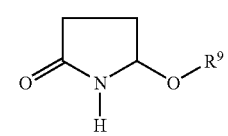

in which

R⁹ is as defined above with metalloaromatic compounds of the formula (IX)

M—Ar² (IX)

in which

Ar² is as defined above and

M represents MgI, MgCl, MgBr, Li or ZnCl, if appropriate in the presence of a diluent (for example diethyl ether, tetrahydrofuran, dioxane or anisol) (cf. Org. Prep. Proced. Int. 1993, 25, 255).

The formula (VI) provides a general definition of the ketocarboxylic acids required as starting materials for carrying out the process (c) according to the invention. In this formula, Ar² preferably, particularly preferably and very particularly preferably has those meanings which have already been mentioned in connection with the description of the starting materials of the formula (II) as being preferred, particularly preferred, etc., for these radicals.

Ketocarboxylic acids of the formula (VI) are known. They can be prepared, for example, by f) reacting aromatic compounds of the formula (VII)

in which

Ar² is as defined above with succinic anhydride or 4-chloro-4-oxobutanoic acid in the presence of a Lewis acid (for example aluminum chloride) and, if appropriate, in the presence of a diluent (for example 1,2-dichloroethane) (cf. Org. Prep. Proced. Int. 1995, 27, 550)

or g) for aromatic compounds which do not allow Friedel-Crafts acylation, alternatively using a corresponding metalloorganic derivative (for example a Grignard reagent) (cf. Syn. Commun. 1996, 26, 3897)

or h) reacting α,β-unsaturated carbonyl compounds of the formula (X)

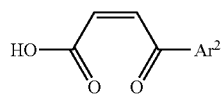

in which

Ar² is as defined above in the presence of a reducing agent (for example Zn dust) and, if appropriate, in the presence of a diluent (for example glacial acetic acid) (cf. Chem. Pharm. Bull. 1988, 36, 2050).

The formula (VII) provides a general definition of the hemi-aminals required as starting materials for carrying out the processes (d) and (e) according to the invention. In this formula, R⁹ preferably represents $C_1$-$C_6$-alkyl or $C_1$-$C_4$-alkylcarbonyl. R⁹ particularly preferably represents $C_1$-$C_4$-alkyl, methylcarbonyl or t-butylcarbonyl. R⁹ very particularly preferably represents methyl, ethyl, i-propyl, t-butyl or methylcarbonyl.

Hemi-aminals of the formula (VII) are known and/or can be prepared by the known processes (cf. Tetrahedron 1975, 31, 1437; Heterocycles 1983, 20, 985).

The formula (VIII) provides a general definition of the aromatic compounds required as starting materials for carrying out the processes (d) and (f) according to the invention. In this formula, Ar² preferably, particularly preferably and very particularly preferably has those meanings which have already been mentioned in connection with the description of the starting materials of the formula (II) as being preferred, particularly preferred, etc., for these radicals.

Aromatic compounds of the formula (VIII) are known.

The formula (IX) provides a general definition of the metalloaromatic compounds required as starting materials for carrying out the process (e) according to the invention. In this formula, Ar² preferably, particularly preferably and very particularly preferably has those meanings which have already been mentioned in connection with the description of the starting materials of the formula (II) as being preferred, particularly preferred, etc., for these radicals. M preferably represents MgI, MgCl, MgBr, Li or ZnCl. M particularly preferably represents MgI, MgCl, MgBr or Li. M very particularly preferably represents MgCl, MgBr or Li.

Metalloaromatic compounds of the formula (IX) are known and/or can be prepared by known methods (for example lithiation or Grignard reaction) from the corresponding aromatic compounds or halogenated aromatic compounds.

The formula (X) provides a general definition of the carbonyl compounds required as starting materials for carrying out the process (h) according to the invention. In this formula, Ar² preferably, particularly preferably and very particularly preferably has those meanings which have already been mentioned in connection with the description of the starting materials of the formula (II) as being preferred, particularly preferred, etc., for these radicals.

Carbonyl compounds of the formula (X) are known. They can be prepared, for example, by i) reacting acetophenones of the formula (XI)

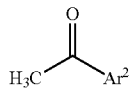

in which

Ar² is as defined above with glyoxalic acid in the presence of a base (for example sodium hydroxide) and, if appropriate, in the presence of a diluent (for example water or ethanol) (cf. J. Med. Chem. 1996, 39, 4396).

The formula (XI) provides a general definition of the acetophenones required as starting materials for carrying out the process (i) according to the invention. In this formula, Ar² preferably, particularly preferably and very particularly preferably has those meanings which have already been mentioned in connection with the description of the starting materials of the formula (II) as being preferred, particularly preferred, etc., for these radicals.

Acetophenones of the formula (XI) are known.

The process according to the invention is carried out in the presence of an acid. Suitable acids for carrying out the process according to the invention are all customary protic acids or strong organic acids (such as, for example, sulfonic acids) or halocarboxylic acids which can be used for such reaction. Preference is given to using hydrochloric acid, sulfuric acid, hydrofluoric acid, phosphoric acid, p-toluenesulfonic acid, methanesulfonic acid, trifluoroacetic acid or trichloroacetic acid.

Particular preference is given to using hydrochloric acid, sulfuric acid p-toluenesulfonic acid or trifluoroacetic acid, very particularly preferably sulfuric acid. If appropriate, the acid used can be employed in a mixture with water. If appropriate, the process according to the invention can be carried out in the presence of a diluent. Suitable diluents for carrying out the process according to the invention are organic acids. Preference is given to using propionic acid, acetic acid or formic acid. Particular preference is given to using acetic acid.

When carrying out the process according to the invention, very particular preference is given to using any mixture of sulfuric acid (as acid) and acetic acid (as diluent) and, if appropriate, water. Particularly suitable is a mixture of concentrated sulfuric acid, water and acetic acid in a ratio of 1:1:2 (volume/volume/volume=v/v/v) or 1:1:3 (v/v/v). However, it is also possible to adjust and employ other mixing ratios.

When carrying out the process according to the invention, the reaction temperatures can be varied within a relatively wide range. In general, the process is carried out at temperatures between 20° C. and 200° C., preferably at temperatures between 60° C. and 150° C.

Expediently, the course of the reaction is monitored by thin-layer chromatography. Depending on the nature of the compound of the formula (II) employed, the reaction time is between 0.5 h and 6 h.

When carrying out the process according to the invention, in general an excess of acid (between 1 mol and 50 mol) is employed per mole of aroylpyrrolidinone of the formula (II). However, it is also possible to choose other ratios of the reaction components. Work-up is carried out by customary methods. In general, the reaction mixture is made alkaline with sodium hydroxide, the product is extracted and the organic phase is washed, dried and concentrated under reduced pressure. The crude product is then freed of any residues that may still be present using customary methods (for example chromatography or recrystallization).

Some of the 2,5-bisaryl-$\Delta^1$-pyrrolines of the formula (I), which can be prepared by the process according to the invention are known. Also known is their use for controlling pests. They are particularly suitable for controlling insects, arachnids and nematodes encountered in agriculture, in forests, in the protection of stored products and materials and in the hygiene sector (see WO 00/21958, WO 99/59968, WO 99/59967 and WO 98/22438).

If the starting materials used are compounds of the formula (II-b), novel insecticidally active $\Delta^1$-pyrrolines of the formula (I-b)

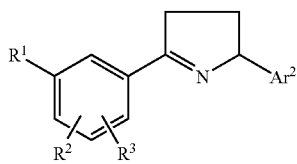

(I-b)

in which

Ar², R¹, R² and R³ have the general, preferred, particularly preferred or very particularly preferred meanings given above are obtained.

If the starting materials used are compounds of the formula (II-c), novel insectidally active $\Delta^1$-pyrrolines of the formula (I-c)

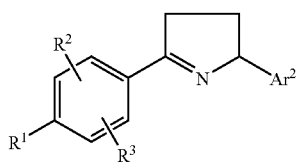

(I-c)

in which

Ar², R¹, R² and R³ have the general, preferred, particularly preferred or very particularly preferred meanings given above are obtained.

If the starting materials used are compounds of the formula (II-d), novel insecticidally active $\Delta^1$-pyrrolines of the formula (I-d)

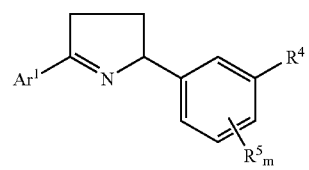

(I-d)

in which

Ar¹, R⁴, R⁵ and m have the general, preferred, particularly preferred or very particularly preferred meanings given above are obtained.

If the starting materials used are compounds of the formula (II-e), novel insecticidally active $\Delta^1$-pyrrolines of the formula (I-e)

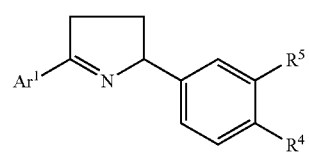

(I-e)

in which

Ar¹, R⁴ and R⁵ have the general, preferred, particularly preferred or very particularly preferred meanings given above are obtained.

If the starting materials used are compounds of the formula (II-f), novel insecticidally active $\Delta^1$-pyrrolines of the formula (I-f)

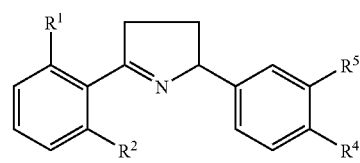

(I-f)

in which

R¹ represents halogen, methyl, methoxy, trifluoromethyl or trifluoromethoxy,

R² represents hydrogen or halogen,

R⁴ represents phenyl which is mono- or disubstituted by radicals from the list W¹ or represents heterocyclyl which is mono- or disubstituted from the list W² or represents the grouping —Y—E, R⁵ represents hydrogen or alkoxy and Y, E, W¹ and W² have the general, preferred, particularly preferred and/or very particularly preferred meanings given above are obtained.

Preferably obtained are compounds of the formula (I-f) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or $C_1$-$C_6$-alkoxy and Y, E, $W^1$ and $W^2$ have the general, preferred, particularly preferred and/or very particularly preferred meanings given above.

Particularly preferably obtained are compounds of the formula (I-f) in which $R^1$ represents fluorine, chlorine, methyl, methoxy, trifluoromethyl or trifluoromethoxy, $R^2$ represents hydrogen, fluorine or chlorine, $R^4$ represents phenyl which is mono- or disubstituted by radicals from list $W^1$ or represents heterocyclyl which is mono- or disubstituted from the list $W^2$ or represents the grouping —Y—E, $R^5$ represents hydrogen, methoxy or ethoxy and Y, E, $W^1$ and $W^2$ have the general, preferred, particularly preferred and/or very particularly preferred meanings given above.

If the starting materials used are compounds of the formula (II-g), novel insecticidally active $\Delta^1$-pyrrolines of the formula (I-g)

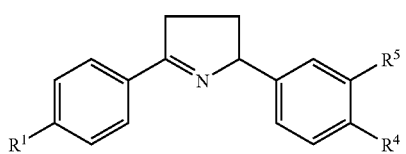

(I-g)

in which $R^1$ represents halogen, methyl, methoxy, trifluoromethyl or trifluoromethoxy, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or alkoxy and Y, E, $W^1$ and $W^2$ have the general, preferred, particularly preferred and/or very particularly preferred meanings given above are obtained.

Preferably obtained are compounds of the formula (I-g) in which $R^1$ represents fluorine, chlorine, methyl, methoxy, trifluoromethyl or trifluoromethoxy, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen or $C_1$-$C_6$-alkoxy and Y, E, $W^1$ and $W^2$ have the general, preferred, particularly preferred and/or very particularly preferred meanings given above.

Particularly preferably obtained are compounds of the formula (I-g) in which $R^1$ represents fluorine, chlorine, methyl, methoxy, trifluoromethyl or trifluoromethoxy, $R^4$ represents phenyl which is mono- or disubstituted by radicals from the list $W^1$ or represents heterocyclyl which is mono- or disubstituted from the list $W^2$ or represents the grouping —Y—E, $R^5$ represents hydrogen, methoxy or ethoxy and Y, E, $W^1$ and $W^2$ have the general, preferred, particularly preferred and/or very particularly preferred meanings given above.

Novel $\Delta^1$-pyrrolines of the formulae mula (I-b), mula (I-c), mula (I-d), (I-e), (I-f) and (I-g) which can be obtained, for example, by the process according to the invention are also claimed according to the invention.

The practice of the process according to the invention is illustrated by the examples below.

PREPARATION EXAMPLES

Example 1

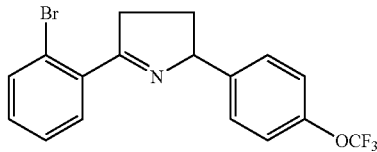

2.1 g (4 mmol) of tert-butyl 3-(2-bromobenzoyl)-2-oxo-5-[4-(trifluoromethoxy)phenyl]-1-pyrrolidinecarboxylate (II-1) are boiled at reflux in 15 ml of glacial acetic acid and 5 ml of concentrated sulfuric acid and 5 ml of water for 3.5 h. After cooling, the reaction mixture is made alkaline using dilute sodium hydroxide solution, the product is extracted with dichloromethane and the organic phase is concentrated under reduced pressure. The residue is chromatographed on silica gel (mobile phase: dichloromethane).

This gives 0.95 g (61.8% of theory) of 5-(2-bromophenyl)-2-[4-(trifluoro-methoxy)phenyl]-3,4-dihydro-2H-pyrrole as an oil.

HPLC: log P (pH 2.3)=3.61.

Analogously to example 1, it is possible to obtain the compounds listed in the table below.

| No. | Structure | logP | m.p. (° C.) |
|---|---|---|---|
| 2 | 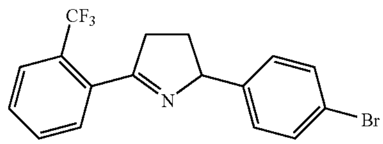 | 3.90[a)] | |
| 3 | 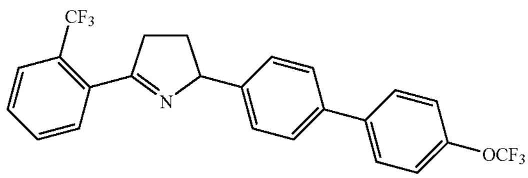 | 5.11[a)] | 56-58 |
| 4 | 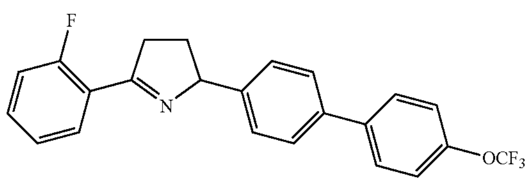 | 3.09[a)] 5.45[b)] | 77-80 |
| 5 | 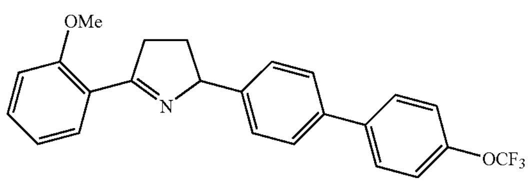 | 2.55[a)] 5.23[b)] | 58-60 |
| 6 | 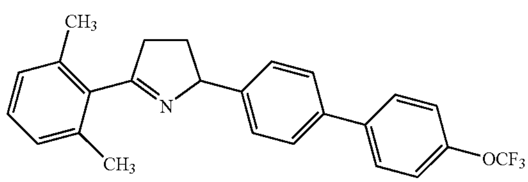 | 5.70[a)] | |
| 7 | 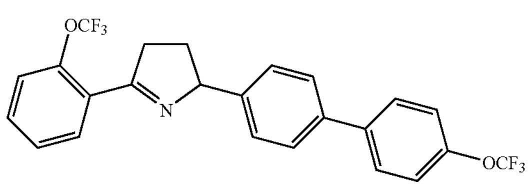 | 4.83[a)] | 42-44 |
| 8 | 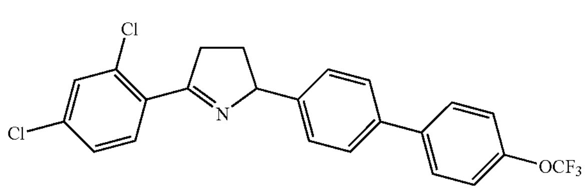 | 5.69[a)] | 68-70 |
| 9 | 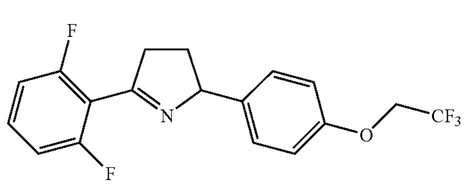 | 2.41[a)] | |

| No. | Structure | logP | m.p. (° C.) |
| --- | --- | --- | --- |
| 10 | 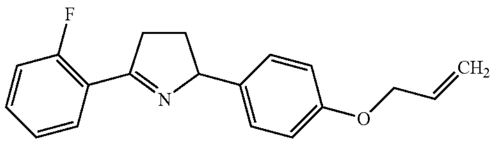 | 1.63[a)] | |
| 11 | 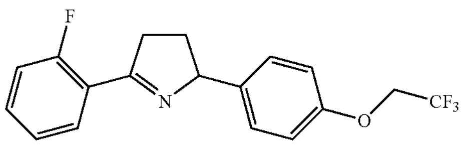 | | |
| 12 | 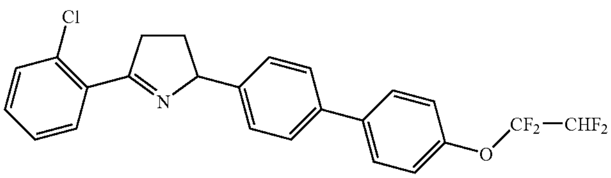 | 3.77[a)] | 80-82 |
| 13 | 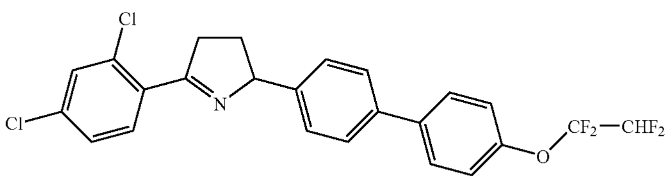 | 5.18[a)] | 78-80 |
| 14 | 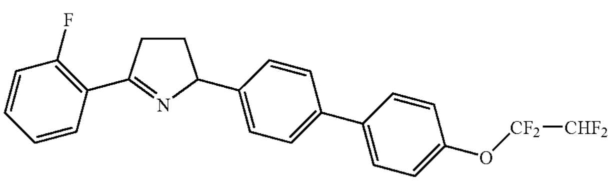 | 2.94[a)] 5.01[b)] | 80 |
| 15 | 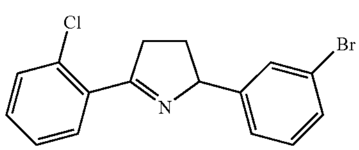 | 2.99[a)] | |
| 16 | 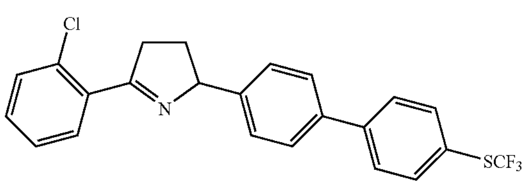 | 4.67[a)] 5.94[b)] | 53-54 |
| 17 | 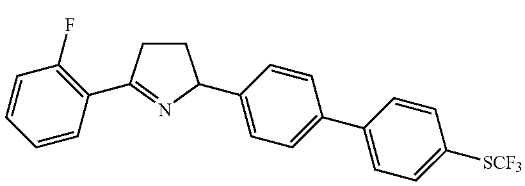 | 3.45[a)] 5.84[b)] | 70-72 |
| 18 | 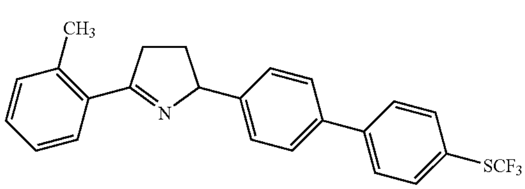 | 3.25[a)] 6.10[b)] | 110-112 |

-continued

| No. | Structure | logP | m.p. (° C.) |
|---|---|---|---|
| 19 | 2,4-dichlorophenyl / pyrroline / biphenyl-SCF₃ | 6.19[a] | 64-66 |
| 20 | 2-chlorophenyl / pyrroline / 4-tert-butylphenyl | 3.05[a] | |
| 21 | 2-chlorophenyl / pyrroline / 4-isopropylphenyl | 2.74[a] | |
| 22 | 2-fluorophenyl / pyrroline / 4-isopropylphenyl | 2.09[a] | |
| 23 | 2-bromophenyl / pyrroline / 4-isopropylphenyl | 3.06[a] | |
| 24 | 2-fluorophenyl / pyrroline / 4-tert-butylphenyl | 2.33[a] 5.06[b] | |
| 25 | 2-methylphenyl / pyrroline / 4-isopropylphenyl | 2.11[a] 5.01[b] | |
| 26 | 2-bromophenyl / pyrroline / 4-tert-butylphenyl | 3.36[a] 5.21[b] | |

-continued

| No. | Structure | logP | m.p. (° C.) |
|---|---|---|---|
| 27 | 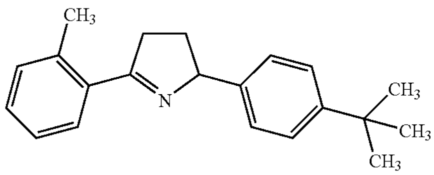 | 2.31[a)] | |
| 28 | 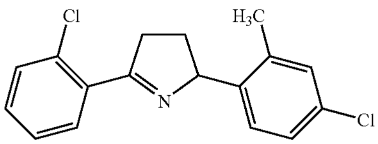 | 3.18[a)]<br>4.62[b)] | |
| 29 | 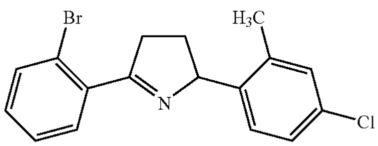 | 3.55[a)]<br>4.63[b)] | |
| 30 | 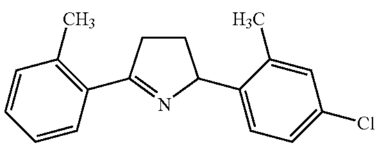 | 2.06[a)]<br>4.79[b)] | |
| 31 | 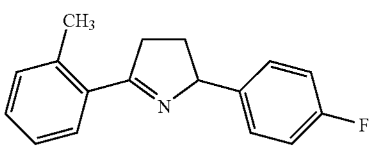 | 1.41[a)] | |
| 32 | 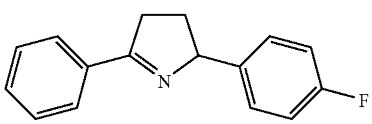 | 1.12[a)]<br>3.34[b)] | 60-61 |
| 33 | 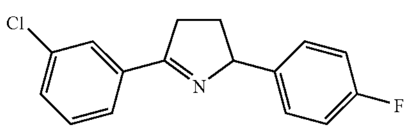 | 1.98[a)]<br>4.05[b)] | 57-59 |
| 34 | 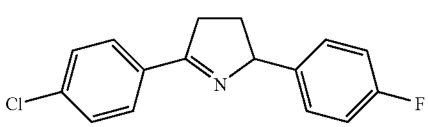 | 1.63[a)]<br>3.99[b)] | 60-62 |
| 35 | 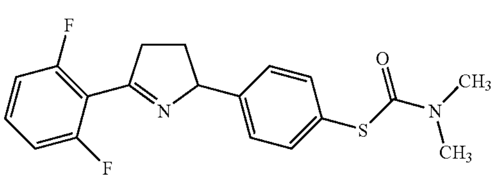 | | 130-140 |
| 36 | 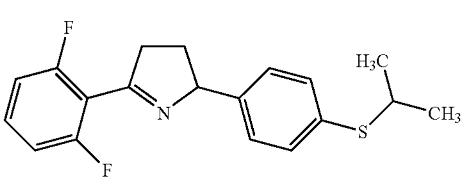 | 2.18[a)] | |

| No. | Structure | logP | m.p. (° C.) |
| --- | --- | --- | --- |
| 37 | 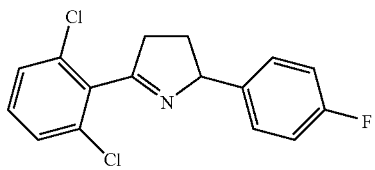 | 3.78[a)]<br>3.95[b)] | |
| 38 | 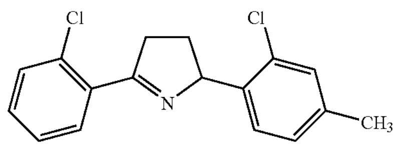 | 3.52[a)]<br>4.86[b)] | |
| 39 | 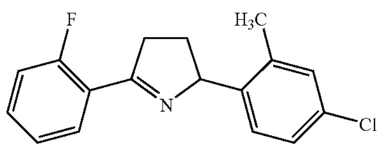 | 2.09[a)]<br>4.51[b)] | |
| 40 | 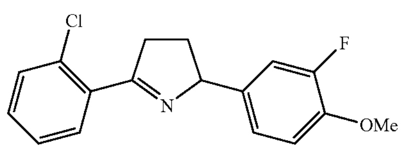 | 1.97[a)]<br>3.52[b)] | |
| 41 | 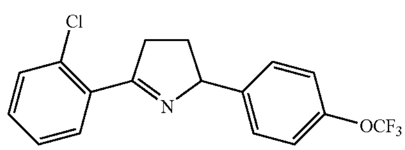 | 4.50[b)] | |
| 42 | 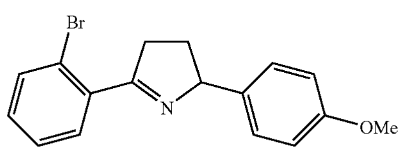 | 1.79[a)]<br>3.50[b)] | |
| 43 | 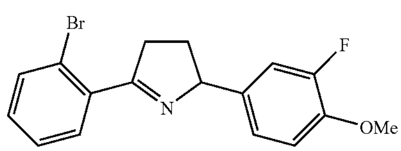 | 2.22[a)] | |
| 44 | 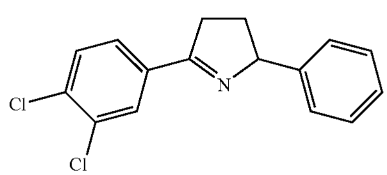 | 2.68[a)]<br>4.59[b)] | |
| 45 | 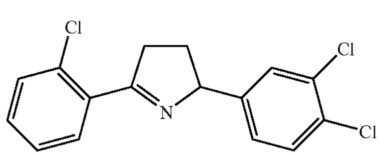 | 3.83[a)]<br>4.75[b)] | |

-continued

| No. | Structure | logP | m.p. (° C.) |
|---|---|---|---|
| 46 | 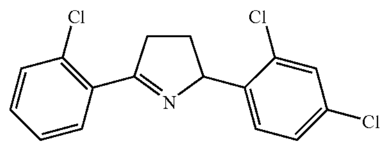 | 4.66[a)]<br>5.20[b)] | |
| 47 | 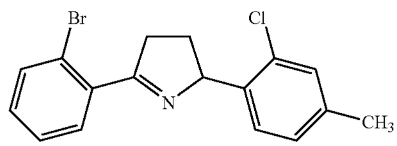 | 3.98[a)]<br>4.88[b)] | |
| 48 | 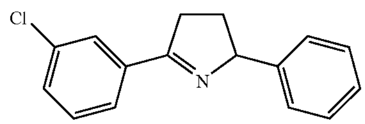 | 1.73[a)]<br>3.97[b)] | |
| 49 | 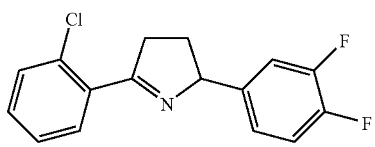 | 2.67[a)]<br>3.86[b)] | |
| 50 | 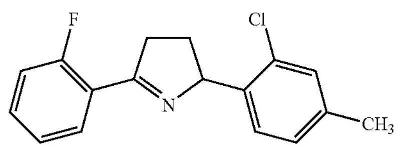 | 2.39[a)]<br>4.74[b)] | |
| 51 | 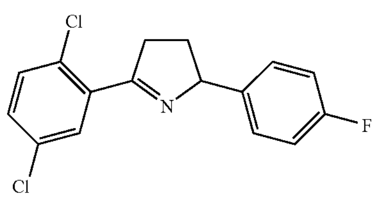 | 3.79[a)]<br>4.36[b)] | |
| 52 | 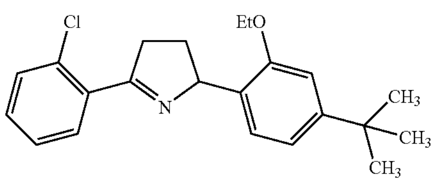 | 3.01[a)]<br>5.78[b)] | |
| 53 | 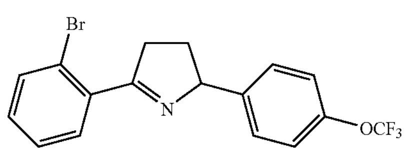 | 3.63[a)] | |
| 54 | 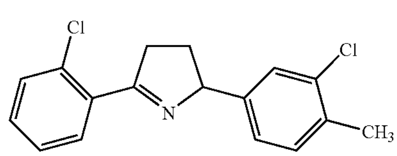 | 2.98[a)]<br>4.67[b)] | |

| No. | Structure | logP | m.p. (° C.) |
|---|---|---|---|
| 55 | 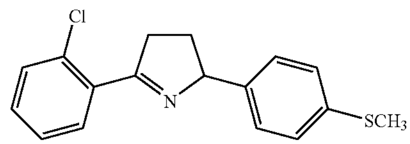 | 2.19[a)] 4.00[b)] | |
| 56 | 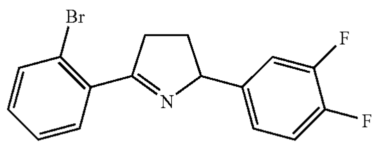 | 3.01[a)] 3.89[b)] | |
| 57 | 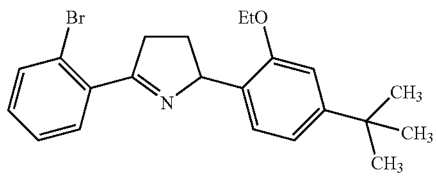 | 3.31[a)] 5.80[b)] | |
| 58 | 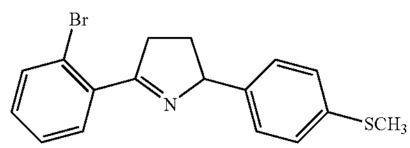 | 2.50[a)] 4.03[b)] | |
| 59 | 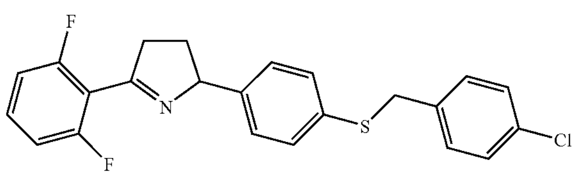 | 2.88[a)] | 112 |
| 60 | 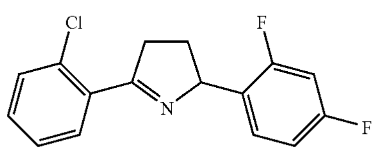 | 2.90[a)] 3.96[b)] | |
| 61 | 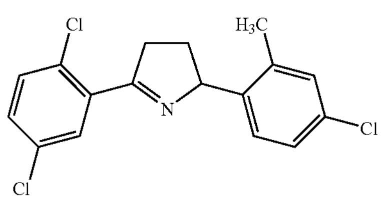 | 5.03[a)] 5.33[b)] | |
| 62 | 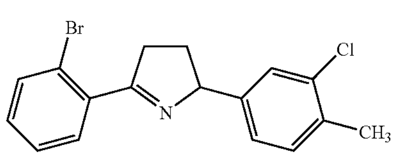 | 3.36[a)] 4.69[b)] | |
| 63 | 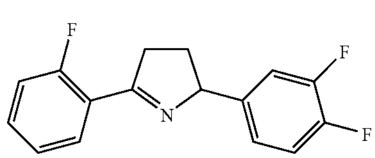 | 1.74[a)] 3.74[b)] | |

-continued
| No. | Structure | logP | m.p. (° C.) |
|---|---|---|---|
| 64 | 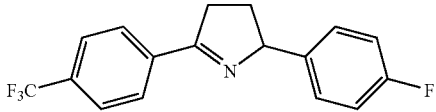 | 2.73[a)]<br>4.20[b)] | |
| 65 | 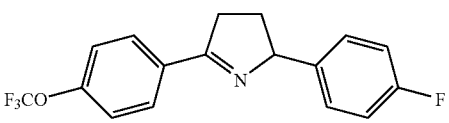 | 2.23[a)]<br>4.31[b)] | |
| 66 | 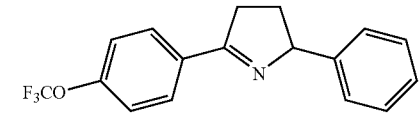 | 2.02[a)]<br>4.26[b)] | |
| 67 | 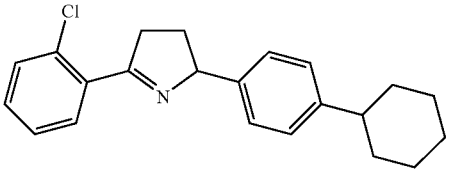 | 6.04[b)] | |
| 68 | 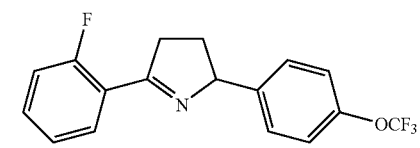 | 4.41[b)] | |
| 69 | 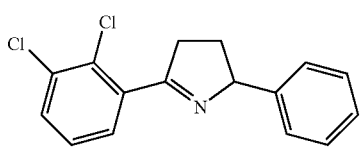 | 4.07[b)] | |
| 70 | 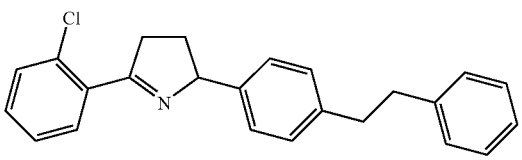 | 3.47[a)]<br>5.33[b)] | |
| 71 | 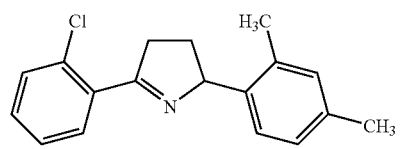 | 2.82[a)]<br>4.45[b)] | |
| 72 | 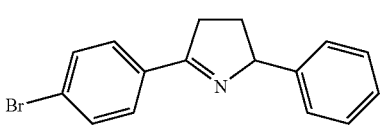 | 1.59[a)]<br>4.06[b)] | 115-16 |
| 73 | 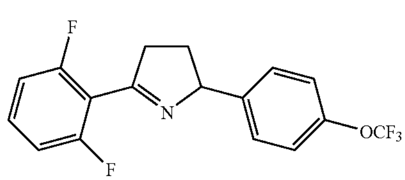 | 4.13[b)] | |

-continued
| No. | Structure | logP | m.p. (° C.) |
|---|---|---|---|
| 74 | 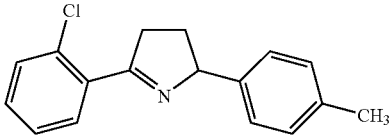 | 1.96[a)]<br>4.04[b)] | |
| 75 | 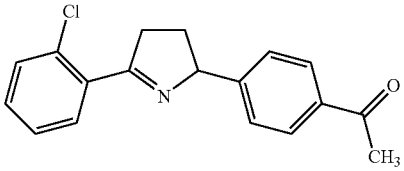 | 1.88[a)]<br>3.06[b)] | |
| 76 | 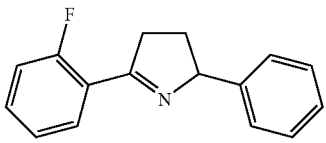 | 1.16[a)]<br>3.45[b)] | |
| 77 | 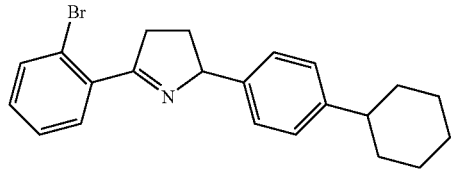 | 4.23[a)]<br>6.03[b)] | |
| 78 | 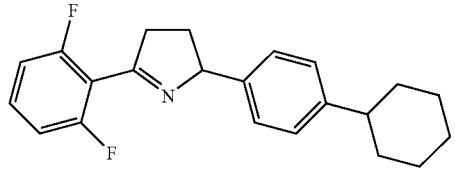 | 3.84[a)]<br>5.56[b)] | |
| 79 | 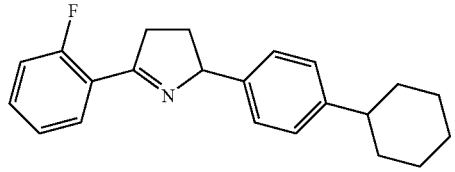 | 2.86[a)]<br>5.95[b)] | 85-87 |
| 80 | 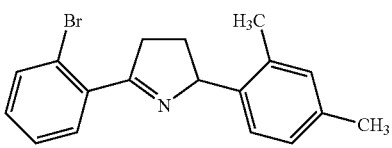 | 2.55[a)]<br>4.46[b)] | |
| 81 | 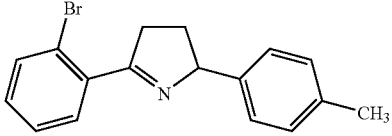 | 2.17[a)]<br>4.07[b)] | |
| 82 | 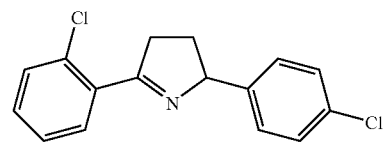 | 2.60[a)]<br>4.23[b)] | |

-continued

| No. | Structure | logP | m.p. (° C.) |
|---|---|---|---|
| 83 | 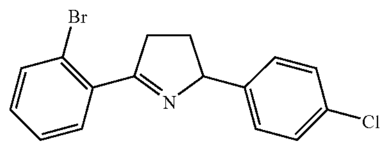 | 2.96[a)]<br>4.22[b)] | |
| 84 | 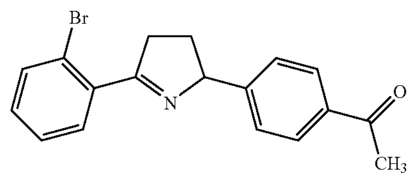 | 2.14[a)]<br>3.09[b)] | |
| 85 | 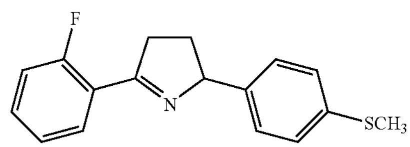 | 1.62[a)]<br>3.88[b)] | |
| 86 | 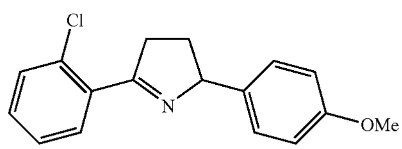 | 1.66[a)]<br>3.47[b)] | |
| 87 | 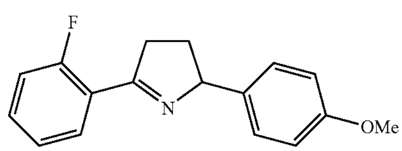 | 1.21[a)]<br>3.32[b)] | |
| 88 | 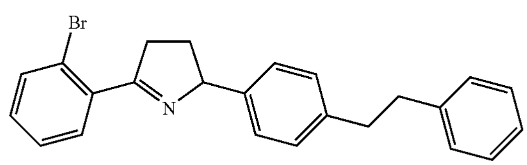 | 3.77[a)]<br>5.35[b)] | |
| 89 | 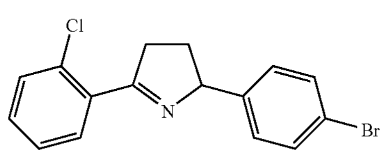 | 2.76[a)]<br>4.36[b)] | |
| 90 | 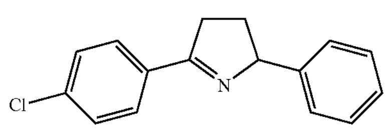 | 1.43[a)] | 84 |
| 91 | 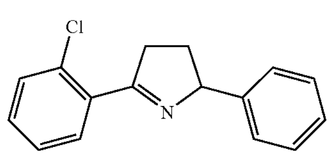 | 1.64[a)]<br>3.61[b)] | |
| 92 | 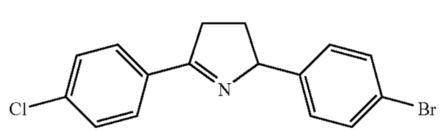 | 2.17[a)] | 96 |

-continued

| No. | Structure | logP | m.p. (° C.) |
|---|---|---|---|
| 93 | 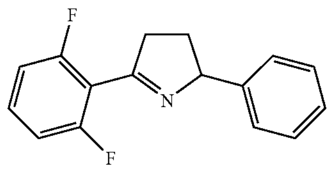 | 1.75[a)] | |
| 94 | 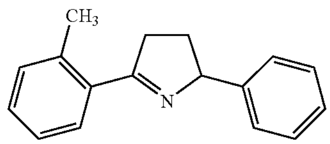 | 1.29[a)]<br>3.70[b)] | |
| 95 | 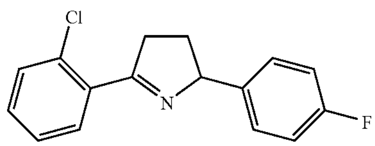 | 2.00[a)]<br>3.68[b)] | |
| 96 | 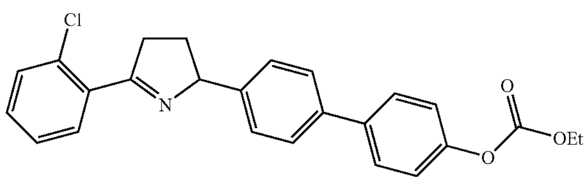 | 3.14[a)] | |
| 97 | 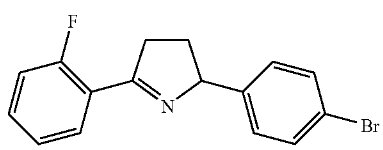 | 1.83[a)] | |
| 98 | 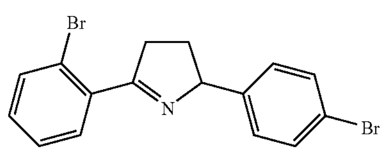 | 3.11[a)] | |
| 99 | 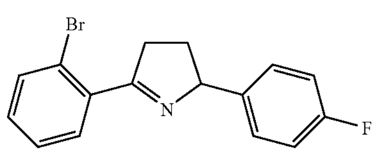 | 2.18[a)] | |
| 100 | 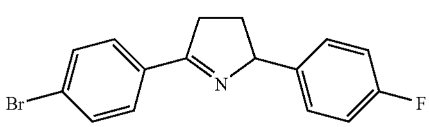 | 1.73[a)]<br>4.14[b)] | 68-70 |
| 101 | 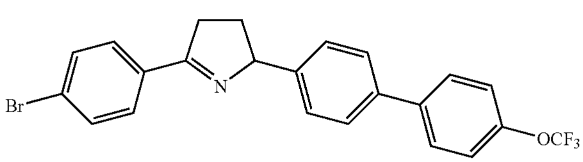 | 3.51[a)]<br>5.95[b)] | 132-134 |

-continued

| No. | Structure | logP | m.p. (° C.) |
|---|---|---|---|
| 102 | 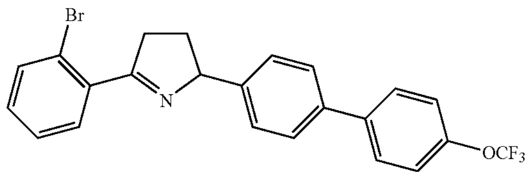 | 4.52[a)]<br>5.56[b)] | 55-57 |
| 103 | 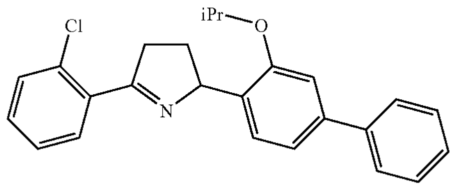 | 3.26[a)] | |
| 104 | 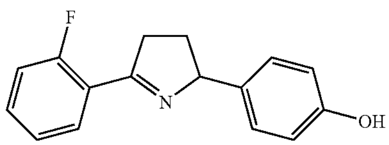 | 0.59[a)] | 110 |
| 105 | 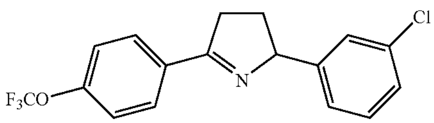 | 4.87[a)] | |
| 106 | 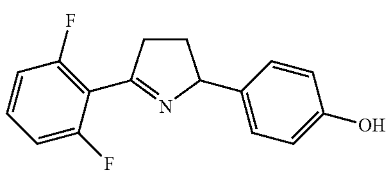 | 0.91[a)] | |
| 107 | 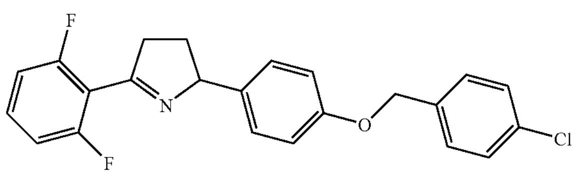 | 3.26[a)] | |
| 108 | 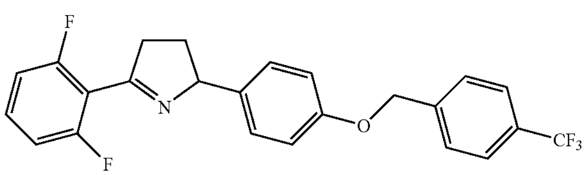 | 3.41[a)] | 70 |
| 109 | 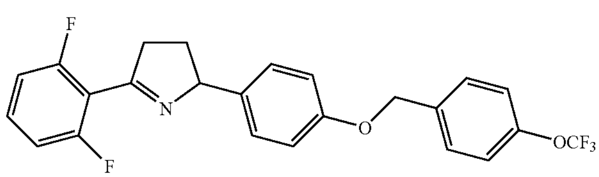 | 3.61[a)] | 74 |
| 110 | 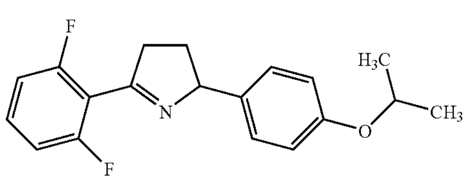 | 2.14[a)] | |

-continued

| No. | Structure | logP | m.p. (° C.) |
|-----|-----------|------|-------------|
| 111 | 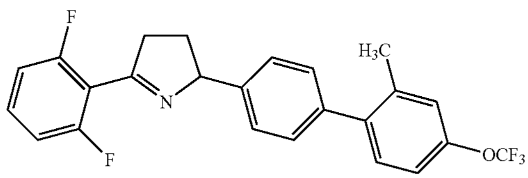 | 4.55[a] | |
| 112 | 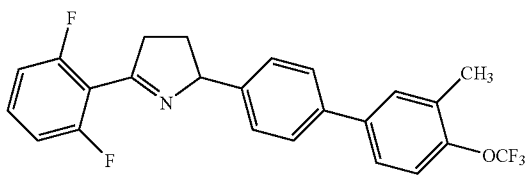 | 4.57[a] | |
| 113 | 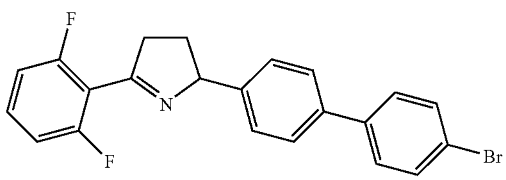 | 3.98[a] | |
| 114 | 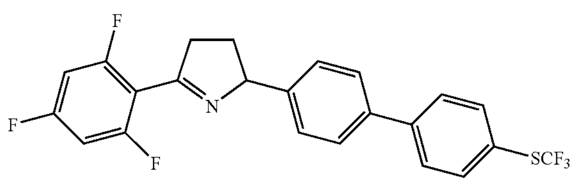 | 5.05[a] | |
| 115 | 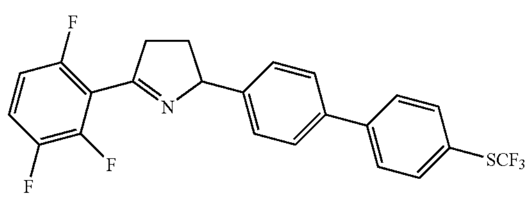 | 5.46[a] | |
| 116 | 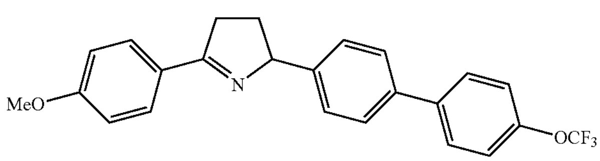 | 2.94[a] | |
| 117 | 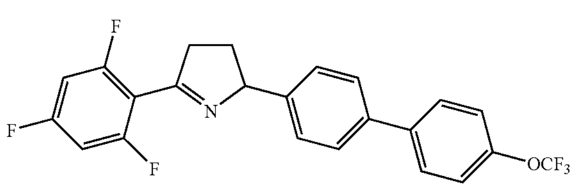 | 4.57[a] | |
| 118 | 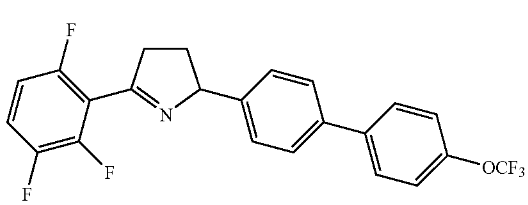 | 5.05[a] | |

-continued

| No. | Structure | logP | m.p. (° C.) |
|---|---|---|---|
| 119 | 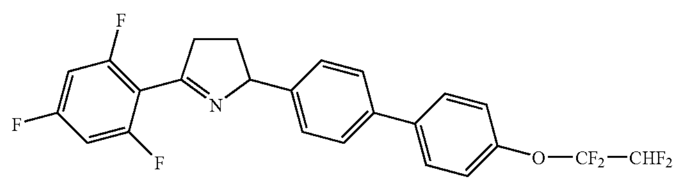 | 4.17[a)] | |
| 120 | 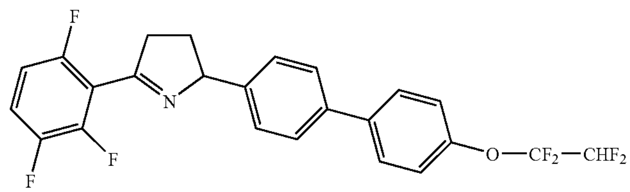 | 4.63[a)] | |

Preparation of Starting Materials of the Formula (II)

Example (II-1)

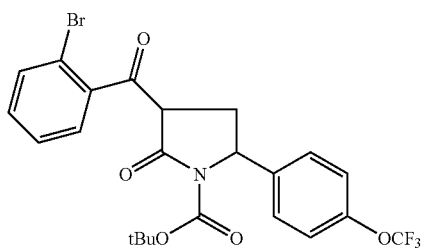
(II-1)

At −50° C., 12 ml (11.6 mmol) of a 1 molar solution of lithium bis(trimethylsilyl)amide in tetrahydrofuran are added dropwise to a solution of 2.0 g (5.8 mmol) of tert-butyl 2-oxo-5-[4-(trifluoromethoxy)phenyl]-1-pyrrolidinecarboxylate (III-1) in 30 ml of tetrahydrofuran and 1.15 g (6.5 mmol) of hexamethylphosphoric triamide. After 10 min of stirring at −50° C., 1.4 g (6.4 mmol) of 2-bromobenzoyl chloride (dissolved in 5 ml of tetrahydrofuran) are then added, and the reaction mixture is allowed to warm to room temperature over a period of 16 h. The mixture is poured into water, acidifed with dilute hydrochloric acid and extracted with dichloromethane. The organic phase is separated off and concentrated under reduced pressure. The residue is triturated with pentane/ethyl acetate and filtered off with suction.

This gives 2.3 g (75.1% of theory) of 3-(2-bromobenzoyl)-2-oxo-5-[4-(trifluoro-methoxy)phenyl]-1-pyrrolidinecarboxylate.

m.p.: 113° C.

HPLC: log P (pH 7.5)=3.35.

In general, compounds of the formula (II) are directly reacted further, without purification.

Analogously to example (II-1), it is possible to obtain the compounds listed in the table below.

| No. | Structure | logP | m.p. (° C.) |
|---|---|---|---|
| II-2 | 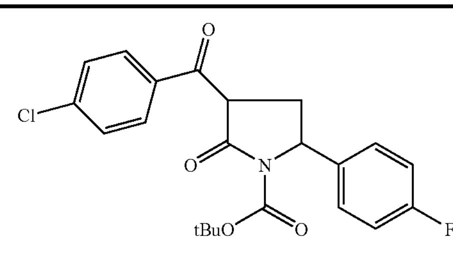 | 4.13[a)] | 160-162 |
| II-3 | 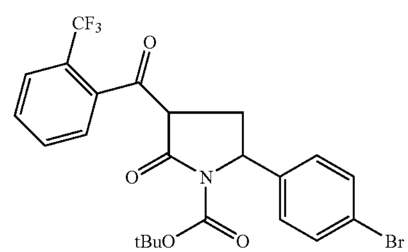 | 3.03[b)] | |

| No. | Structure | logP | m.p. (° C.) |
|---|---|---|---|
| II-4 | 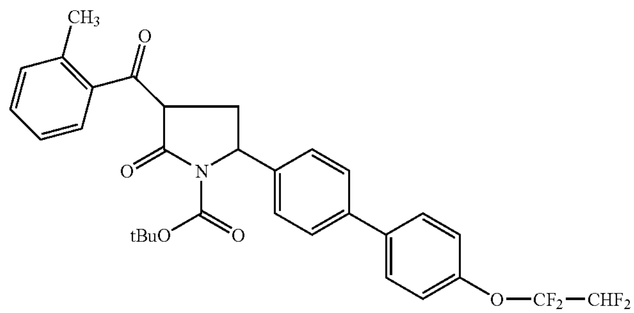 | 5.51[b] | 80-86 |
| II-5 | 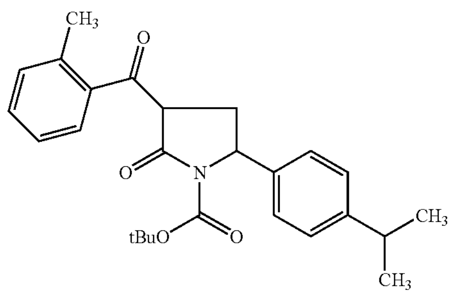 | 5.05[b] | |
| II-6 | 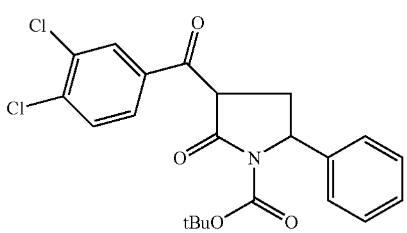 | 4.60[b] | 134-136 |

Preparation of Starting Materials of the Formula (III)

Example (III-1)

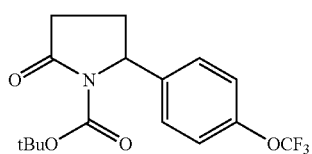

(III-1)

13.6 g (55 mmol) of 5-[4-(trifluoromethoxy)phenyl]-2-pyrrolidinone (V-1) in 60 ml of dimethylformamide are, with addition of 0.4 g of dimethylaminopyridine, stirred with 27.6 g (0.13 mol) of di-tert-butyl dicarbonate at 20° C. for 16 h. Most of the solvent is then removed, and the residue is partitioned between water and dichloromethane. The organic phase is again washed with water and concentrated under reduced pressure. The residue is triturated with pentane and filtered off with suction.

This gives 13.7 g (72.1% of theory) of tert-butyl 2-oxo-5-[4-(trifluoromethoxy)phenyl]-1-pyrrolidinecarboxylate.

m.p.: 120° C.

HPLC: log P (pH 2.3)=3.28.

Analogously to example (III-1), it is possible to obtain the compounds listed in the table below. Purification is either as described in the example or by recrystallization or by chromatography.

| No. | Structure | logP | m.p. (° C.) |
|---|---|---|---|
| III-2 | 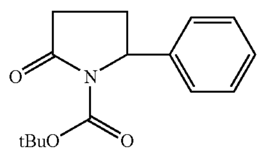 | 2.52[a] | 92-94 |
| III-3 | 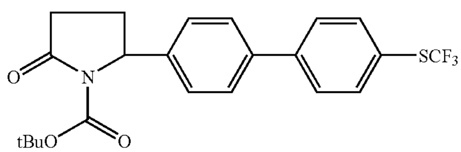 | 4.67[a] | 150-152 |
| III-4 | 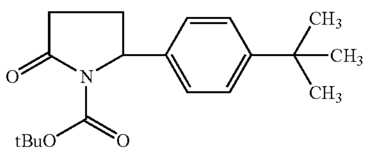 | 3.92[a] | 121 |
| III-5 | 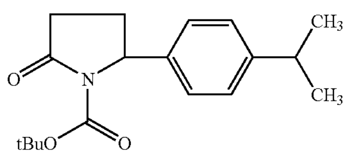 | 3.65[a] | 110 |
| III-6 | 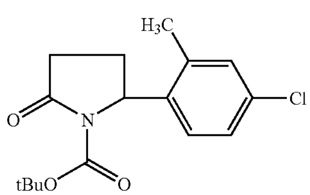 | 3.24[a]<br>3.25[b] | 110-112 |
| III-7 | 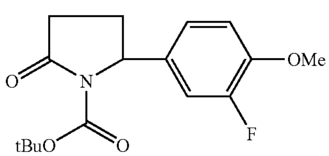 | 2.43[a] | 113-115 |
| III-8 | 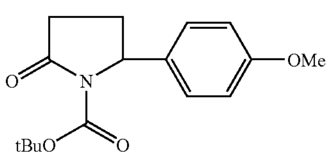 | 2.43[a] | 64-65 |
| III-9 | 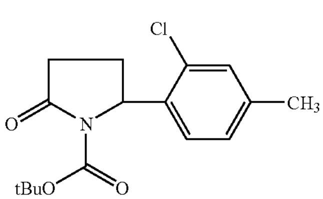 | 3.83[a] | 96-97 |
| III-10 | 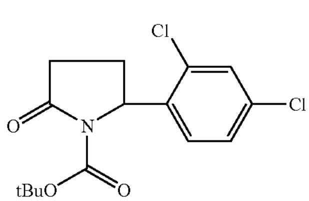 | 3.54[a] | 99-100 |

-continued

| No. | Structure | logP | m.p. (° C.) |
|---|---|---|---|
| III-11 | 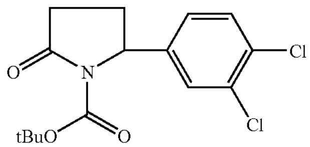 | 3.29[a] | 124-127 |
| III-12 | 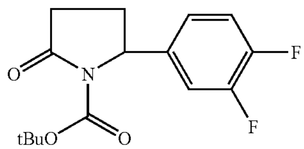 | 2.67[a] | 120-122 |
| III-13 | 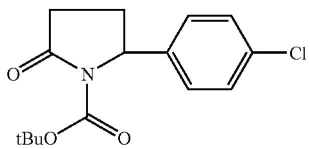 | 2.93[a] | 134-136 |
| III-14 | 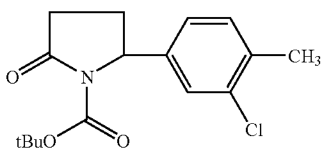 | 3.30[a] | 119-120 |
| III-15 | 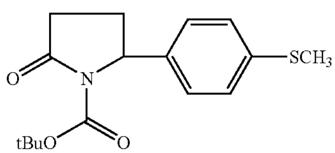 | 2.84[a]<br>2.83[b] | 120 |
| III-16 | 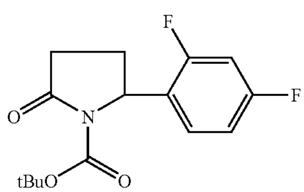 | 2.69[a] | 85-87 |
| III-17 | 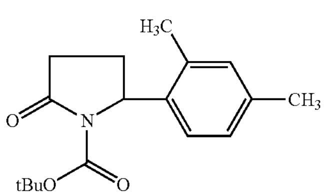 | 3.20[a] | 60-62 |
| III-18 | 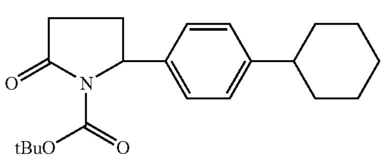 | 4.71[a] | 119-120 |
| III-19 | 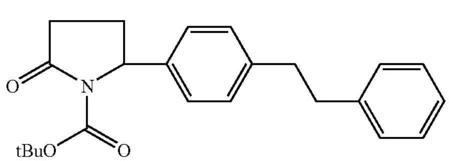 | 4.11[a] | 118-23 |

-continued

| No. | Structure | logP | m.p. (° C.) |
|---|---|---|---|
| III-20 | 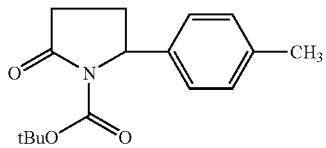 | 2.90[a)] | 85-87 |
| III-21 | 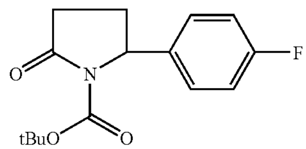 | 2.57[a)] | 117 |
| III-22 | 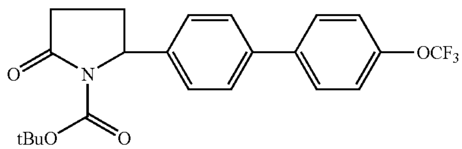 | 4.32[a)] | 130 |
| III-23 | 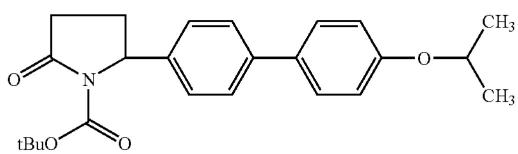 | 4.17[a)] | 166 |
| III-24 | 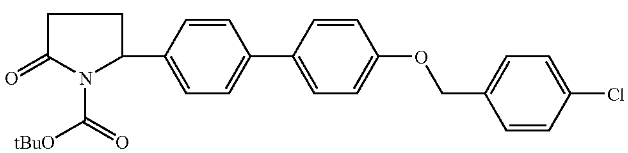 | 4.93[a)] | 152 |
| III-25 | 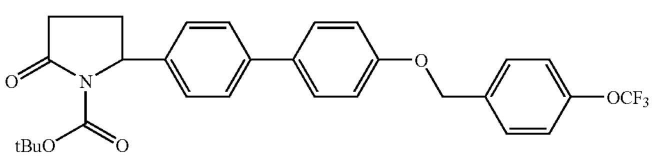 | 5.03[a)] | 132 |
| III-26 | 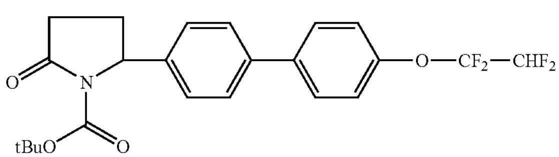 | 3.85[a)] | |
| III-27 | 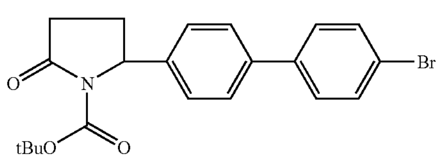 | 4.26[a)] | 163-164 |
| III-28 | 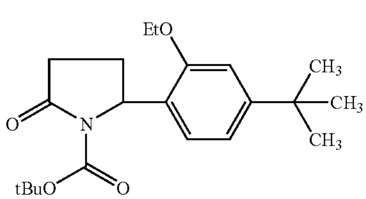 | 4.40[a)] | |

Preparation of Starting Materials of the Formula (V)

Example (V-1)

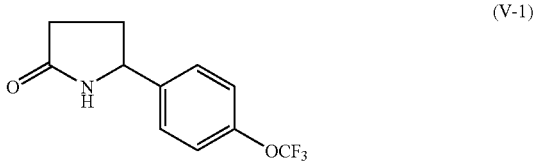
(V-1)

With 70 ml of liquid ammonia and 2 g of Raney nickel, 19.0 g (72 mmol) of 3-(4-trifluoromethoxybenzoyl)propionic acid in 170 ml of ethanol are, under a hydrogen pressure of 150 bar, heated at 150° C. for 3 h. After cooling, the catalyst is filtered off, the solvent is removed under reduced pressure and the residue is triturated with pentane.

This gives 14.4 g (81.7% of theory) of 5-[4-(trifluoromethoxy)phenyl]-2-pyrrolidinone of melting point 105-106° C.

HPLC: logP (pH 2.3)=2.00.

Example (V-2)

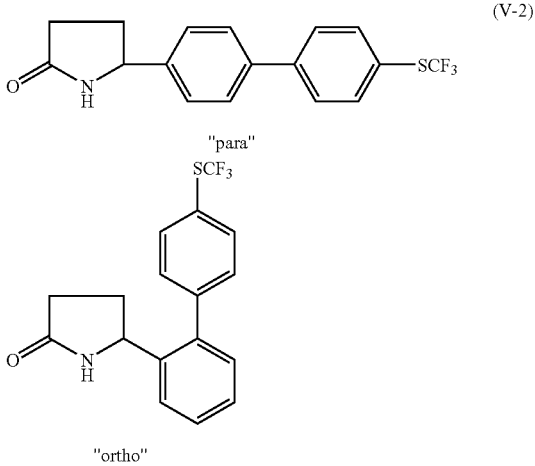
(V-2)

"para"

"ortho"

Hydrogen fluoride (2500 ml) is initially charged at 0° C. A solution of 5-ethoxy-2-pyrrolidinone (264 g, 2.04 mol) and 4-[(trifluoromethyl)thio]-1,1'-biphenyl (260 g, 1.02 mol) in dichloromethane (400 ml) is added dropwise. The reaction mixture is then stirred at room temperature, and the hydrogen fluoride is finally removed under reduced pressure. The residue is taken up in dichloromethane and washed with saturated aqueous sodium bicarbonate solution. The organic phase is dried over magnesium sulfate, filtered and concentrated. The crude products of two batches are combined and initially stirred with toluene. The crude product is then purified by silica gel chromatography (mobile phase: ethyl acetate/ethanol 7:3 v/v).

This gives off 5-{4'-[(trifluoromethyl)thio]-1,1'-biphenyl-4-yl}-2-pyrrolidinone "para" isomer: 173.2 g (25% of theory)

HPLC: log P (pH 2.3)=3.24 (99.5% purity) "ortho" isomer: 27.6 g (4% of theory)

HPLC: log P (pH 2.3)=3.15 (98.6% purity)

Example (V-3)

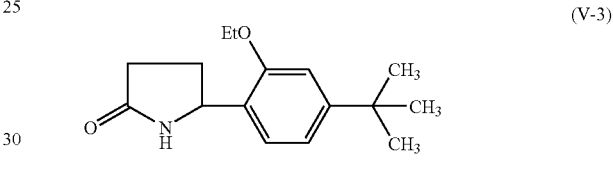
(V-3)

5-Ethoxy-2-pyrrolidinone (11.5 g, 0.1 mol) is initially charged at 0° C. in a mixture of glacial acetic acid (89 ml) and concentrated sulfuric acid (10 ml). 1-Tert-butyl-3-ethoxybenzene (19.61 g, 0.11 mol) is added, and the reaction mixture is then stirred at 0° C. for 2 h and at room temperature for 48 h. The reaction mixture is poured onto ice and repeatedly extracted with ethyl acetate. The combined organic phases are washed with aqueous saturated sodium bicarbonate solution, dried over magnesium sulfate, filtered and concentrated.

This gives 23.62 g (75% of theory) of 5-(4-tert-butyl-2-ethoxyphenyl)-2-pyrrolidinone.

HPLC: log P (pH 2.3)=2.84 (83% purity)

Analogously to one of examples (V-1) to (V-3), it is possible to obtain the compounds listed in the table below. Purification is either as described in the example or by recrystallization or by chromatography.

| No. | Structure | logP | m.p. (° C.) |
|---|---|---|---|
| V-4 | ![structure] | 1.90[a] | 157-160 |

-continued
| No. | Structure | logP | m.p. (° C.) |
|---|---|---|---|
| V-5 | 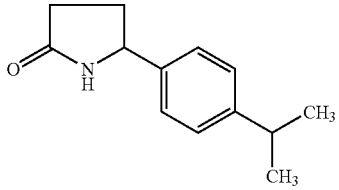 | 2.13[a] | 100-102 |
| V-6 | 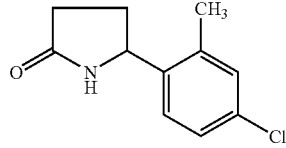 | 1.86[a] | 175-179 |
| V-7 | 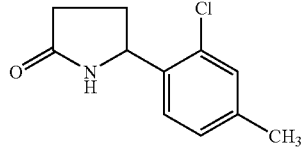 | 1.92[a] | 140-142 |
| V-8 | 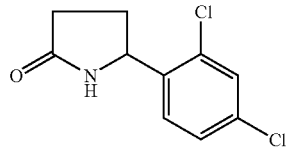 | 2.02[a] | ca. 140 |
| V-9 | 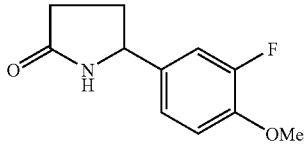 | 1.29[a] | 104-106 |
| V-10 | 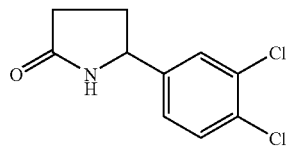 | 1.92[a] | 103-105 |
| V-11 | 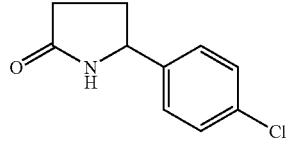 | 1.61[a] | 101-104 |
| V-12 | 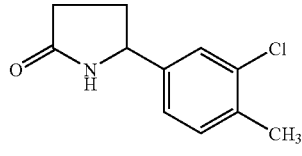 | 1.92[a] | 74-76 |
| V-13 | 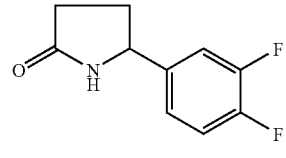 | 1.43[a] | 96 |

-continued

| No. | Structure | logP | m.p. (° C.) |
|---|---|---|---|
| V-14 | 5-(4-methylphenyl)pyrrolidin-2-one | 1.52[a)] | 110–112 |
| V-15 | 5-phenylpyrrolidin-2-one | 1.21[a)] | 104 |
| V-16 | 5-(4-bromophenyl)pyrrolidin-2-one | 1.72[a)] | 138–140 |
| V-17 | 5-(4-fluorophenyl)pyrrolidin-2-one | 1.32[a)] | 124–126 |
| V-18 | 5-(4'-hydroxybiphenyl-4-yl)pyrrolidin-2-one | 1.47[a)] | 296 |
| V-19 | 5-(4-hydroxyphenyl)pyrrolidin-2-one | 0.55[a)] | 218 |
| V-20 | 5-[4'-(ethoxycarbonyloxy)biphenyl-4-yl]pyrrolidin-2-one | 2.39[a)] | 178 |
| V-21 | 5-[4'-isopropoxybiphenyl-4-yl]pyrrolidin-2-one | 2.77[a)] | 140 |
| V-22 | 5-[4'-(4-chlorobenzyloxy)biphenyl-4-yl]pyrrolidin-2-one | 3.62[a)] | 210 |
| V-23 | 5-[4'-(4-trifluoromethoxybenzyloxy)biphenyl-4-yl]pyrrolidin-2-one | 3.83[a)] | 200 |
| V-24 | 5-[4'-(1,1,2,2-tetrafluoroethoxy)biphenyl-4-yl]pyrrolidin-2-one | 2.78[a)] | Decomposition from 187 |

| No. | Structure | logP | m.p. (° C.) |
|---|---|---|---|
| V-25 | 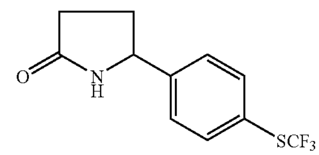 | 1.59[a)] | 161-163 |
| V-26 | 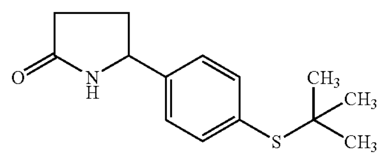 | 2.69[a)] | 68 |
| V-27 | 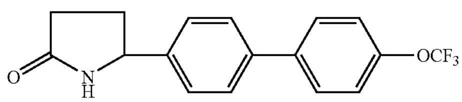 | 2.96[a)] | |
| V-28 | 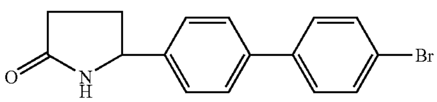 | 2.76[a)] | |

The logP values given in the tables and preparation examples above are determined in accordance with EEC directive 79/831 Annex V.A8 by HPLC (High Performance Liquid Chromatography) on a reverse-phase column (C 18). Temperature: 43° C.

In the acidic range, the determination is carried out at pH 2.3 using the mobile phases 0.1% aqueous phosphoric acid and acetonitrile; linear gradient from 10% acetonitrile to 90% acetonitrile. (In the tables, the measurement values obtained are marked [a)].)

In the neutral range, the determination is carried out at pH 7.5 using the mobile phases 0.01 molar aqueous phosphate buffer solution and acetonitrile; linear gradient from 10% acetonitrile to 90% acetonitrile. (In the tables, the measurement values obtained are marked [b)].)

Calibration is carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

The invention claimed is:

1. A process for preparing a 2,5-bisaryl-Δ$^1$-pyrroline of the Formula (I)

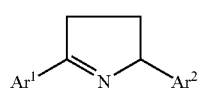

in which

Ar$^1$ represents the radical

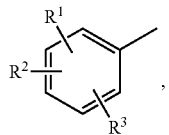

Ar$^2$ represents the radical

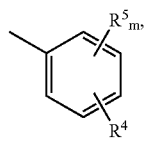

m represents 1, 2, 3 or 4,

R$^1$ represents halogen, cyano, nitro, alkyl, alkoxy, haloalkyl, haloalkoxy, alkoxyalkyl or —S(O)$_o$R$^6$, R$^2$ and R$^3$ independently of one another represent hydrogen, halogen, cyano, nitro, alkyl, alkoxy, haloalkyl, haloalkoxy, alkoxyalkyl or —S(O)$_o$R$^6$, R$^4$ represents halogen or one of the groupings below (l) —X—A (m) —B—Z—D (n) —Y—E R$^5$ represents hydrogen, halogen, hydroxyl, cyano, alkyl, alkylcarbonyl, alkoxy, haloalkyl, haloalkoxy, trialkylsilyl, alkoxycarbonyl, —CONR$^7$R$^8$, —OSO$_2$NR$^7$R$^8$ or —S(O)$_o$R$^6$, X represents a direct bond, O (oxygen), S(O)$_o$, NR$^6$, carbonyl, carbonyloxy, oxycarbonyl, oxysulfonyl (OSO$_2$), alkylene, alkenylene, alkynylene, alkylenoxy, oxyalkylene, oxyalkylenoxy, thioalkylene, cyclopropylene or oxiranylene, A represents phenyl, naphthyl or tetrahydronaphthyl, each of which is optionally mono- or polysubstituted by radicals from the list $W^1$, B represents p-phenylene which is optionally mono- or disubstituted by radicals from the list $W^1$, Z represents $(CH_2)_n$, O (oxygen) or $S(O)_o$, D represents hydrogen, alkyl, alkenyl, alkynyl, haloalkyl, haloalkenyl, alkoxycarbonyl, haloalkylsulfonyl or dialkylaminosulfonyl, Y represents a direct bond, O (oxygen), S (sulfur), $SO_2$, carbonyl, carbonyloxy, oxycarbonyl, alkylene, alkenylene, alkynylene, haloalkylene, haloalkenylene, alkylenoxy, oxyalkylene, oxyalkylenoxy or thioalkylene, E represents hydrogen, alkyl, alkenyl, alkynyl, haloalkyl, haloalkenyl, haloalkylsulfonyl, cycloalkyl, dialkylaminocarbonyl or dialkylaminosulfonyl, $W^1$ represents cyano, halogen, formyl, nitro, alkyl, trialkylsilyl, alkoxy, haloalkyl, haloalkoxy, haloalkenyloxy, haloalkylsulfonyloxy, alkylcarbonyl, alkoxycarbonyl, —$S(O)_oR^6$, —$SO_2NR^7R^8$ or —$OSO_2NR^7R^8$, n represents 0, 1, 2, 3 or 4, o represents 0, 1 or 2, $R^6$ represents hydrogen, alkyl or haloalkyl, $R^7$ and $R^8$ independently of one another represent hydrogen, alkyl, haloalkyl, or together represent alkylene, alkoxyalkylene or alkylthioalkylene, comprising:

reacting an aroylpyrrolidinone of the Formula (II)

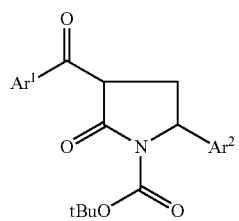

(II)

in which $Ar^1$ and $Ar^2$ are as defined above with an acid, optionally in the presence of a diluent.

2. A process as claimed in claim 1, wherein the aroylpyrrolidinone of the Formula (II) is

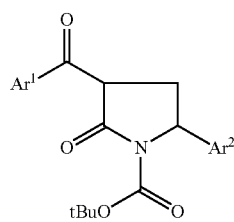

(II)

in which $Ar^1$ represents the radical

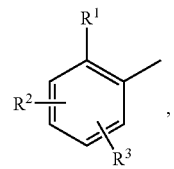

$Ar^2$ represents the radical

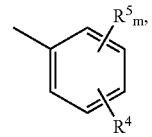

m represents 1, 2 or 3, $R^1$ represents halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkoxyalkyl or —$S(O)_oR^6$, $R^2$ and $R^3$ independently of one another represent hydrogen, halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkoxy-$C_1$-$C_6$-alkyl or —$S(O)_oR^6$, $R^4$ represents fluorine, chlorine, bromine, iodine or one of the groupings below (l) —X—A (m) —B—Z—D (n) —Y—E $R^5$ represents hydrogen, halogen, hydroxyl, cyano, $C_1$-$C_6$-alkyl, $C_1$-$C_6$-alkylcarbonyl, $C_1$-$C_6$-alkoxy, $C_1$-$C_6$-haloalkyl, $C_1$-$C_6$-haloalkoxy, tri($C_1$-$C_6$-alkyl)silyl, $C_1$-$C_6$-alkoxycarbonyl, —$CONR^7R^8$, —$OSO_2NR^7R^8$ or —$S(O)_oR^6$, X represents a direct bond, O (oxygen), $S(O)_o$, $NR^6$, carbonyl, carbonyloxy, oxycarbonyl, oxysulfonyl ($OSO_2$), $C_1$-$C_4$-alkylene, $C_2$-$C_4$-alkenylene, $C_2$-$C_4$-alkynylene, $C_1$-$C_4$-alkylenoxy, $C_1$-$C_4$-oxyalkylene, $C_1$-$C_4$-oxyalkylenoxy, thio-$C_1$-$C_4$-alkylene, cyclopropylene or oxiranylene, A represents phenyl, naphthyl or tetrahydronaphthyl, each of which is optionally mono- to tetrasubstituted by radicals from the list $W^1$, B represents p-phenylene which is optionally mono- or disubstituted by radicals from the list $W^1$, Z represents $(CH_2)_n$, O (oxygen) or $S(O)_o$, D represents hydrogen, $C_1$-$C_6$-alkyl, $C_1$-$C_6$-alkenyl, $C_2$-$C_6$-alkynyl, $C_1$-$C_6$-haloalkyl, $C_2$-$C_6$-haloalkenyl, $C_1$-$C_6$-alkoxycarbonyl, $C_1$-$C_6$-haloalkylsulfonyl or di($C_1$-$C_6$-alkyl)aminosulfonyl, Y represents a direct bond, O (oxygen), S (sulfur), $SO_2$, carbonyl, carbonyloxy, oxycarbonyl, $C_1$-$C_6$-alkylene, $C_2$-$C_6$-alkenylene, $C_2$-$C_6$-alkynylene, $C_1$-$C_6$-haloalkylene, $C_2$-$C_6$-haloalkenylene, $C_1$-$C_4$-alkylenoxy, $C_1$-$C_4$-oxyalkylene, $C_1$-$C_4$-oxyalkylenoxy or thio-$C_1$-$C_4$-alkylene, E represents hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_1$-$C_6$-haloalkylsulfonyl, $C_3$-$C_7$-cycloalkyl, di($C_1$-$C_6$-alkyl)aminocarbonyl or di($C_1$-$C_6$-alkyl)aminosulfonyl, $W^1$ represents cyano, halogen, formyl, nitro, $C_1$-$C_6$-alkyl, $C_1$-$C_4$-tri-alkylsilyl, $C_1$-$C_6$-alkoxy, $C_1$-$C_6$-haloalkyl, $C_1$-$C_6$-haloalkoxy, $C_2$-$C_6$-haloalkenyloxy, $C_1$-$C_6$-haloalkylsulfonyloxy, $C_1$-$C_6$-alkylcarbonyl, $C_1$-$C_6$-alkoxycarbonyl, —S(O)$_o$R$^6$, —SO$_2$NR$^7$R$^8$ or —OSO$_2$NR$^7$R$^8$, n represents 0, 1, 2, 3 or 4, o represents 0, 1 or 2, R$^6$ represents hydrogen, $C_1$-$C_6$-alkyl or $C_1$-$C_6$-haloalkyl, R$^7$ and R$^8$ independently of one another represent hydrogen, $C_1$-$C_6$-alkyl, $C_1$-$C_6$-haloalkyl, or together represent $C_2$-$C_6$-alkylene, $C_1$-$C_4$-alkoxy-$C_1$-$C_4$-alkyl or $C_1$-$C_4$-alkylthio-$C_1$-$C_4$-alkyl.

3. A process as claimed in claim 1, wherein the aroylpyrrolidinone of the Formula (II) is

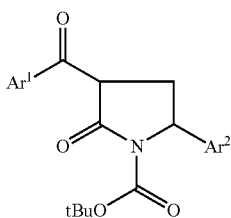
(II)

in which

Ar$^1$ represents the radical

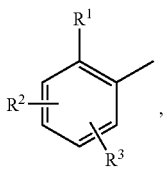,

Ar$^2$ represents the radical

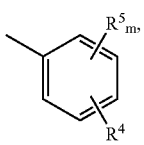

m represents 1 or 2,

R$^1$ represents fluorine, chlorine, bromine, $C_1$-$C_6$-alkyl, $C_1$-$C_6$-alkoxy, $C_1$-$C_6$-haloalkyl having 1 to 13 fluorine and/or chlorine atoms or $C_1$-$C_6$-haloalkoxy having 1 to 13 fluorine and/or chlorine atoms, R$^2$ and R$^3$ independently of one another represent hydrogen, fluorine, chlorine, bromine, $C_1$-$C_6$-alkyl, $C_1$-$C_6$-alkoxy, $C_1$-$C_6$-haloalkyl having 1 to 13 fluorine and/or chlorine atoms or $C_1$-$C_6$-haloalkoxy having 1 to 13 fluorine and/or chlorine atoms, R$^4$ represents fluorine, chlorine, bromine, iodine or one of the groupings below (l) —X—A (m) —B—Z—D (n) —Y—E R$^5$ represents hydrogen, fluorine, chlorine, bromine, hydroxyl, cyano, $C_1$-$C_6$-alkyl, $C_1$-$C_6$-alkylcarbonyl, $C_1$-$C_6$-alkoxy, $C_1$-$C_6$-haloalkyl having 1 to 13 fluorine and/or chlorine atoms, $C_1$-$C_6$-haloalkoxy having 1 to 13 fluorine and/or chlorine atoms or —S(O)$_o$R$^6$, X represents a direct bond, O (oxygen), S (sulfur), SO$_2$, carbonyl, carbonyloxy, oxycarbonyl, oxysulfonyl (OSO$_2$), $C_1$-$C_4$-alkylene, $C_2$-$C_4$-alkenylene, $C_2$-$C_4$-alkynylene, $C_1$-$C_4$-alkylenoxy, $C_1$-$C_4$-oxyalkylene, $C_1$-$C_4$-oxyalkylenoxy, thio-$C_1$-$C_4$-alkylene, cyclopropylene or oxiranylene, A represents phenyl, naphthyl or tetrahydronaphthyl, each of which is optionally mono- to trisubstituted by radicals from the list W$^1$, B represents p-phenylene which is optionally mono- or disubstituted by radicals from the list W$^1$, Z represents (CH$_2$)$_n$, O (oxygen) or S(O)$_o$, D represents hydrogen, $C_1$-$C_6$-alkyl, $C_1$-$C_6$-alkenyl, $C_2$-$C_6$-alkynyl, $C_1$-$C_6$-haloalkyl having 1 to 13 fluorine and/or chlorine atoms, $C_2$-$C_6$-haloalkenyl having 1 to 11 fluorine and/or chlorine atoms, $C_1$-$C_6$-alkoxycarbonyl, $C_1$-$C_6$-haloalkylsulfonyl having 1 to 13 fluorine and/or chlorine atoms or di($C_1$-$C_4$-alkyl)aminosulfonyl, Y represents a direct bond, O (oxygen), S (sulfur), SO$_2$, carbonyl, carbonyloxy, oxycarbonyl, $C_1$-$C_6$-alkylene, $C_2$-$C_6$-alkenylene, $C_2$-$C_6$-alkynylene, $C_1$-$C_6$-haloalkylene having 1 to 12 fluorine and/or chlorine atoms, $C_2$-$C_6$-haloalkenylene having 1 to 10 fluorine and/or chlorine atoms, $C_1$-$C_4$-alkylenoxy, $C_1$-$C_4$-oxyalkylene, $C_1$-$C_4$-oxyalkylenoxy or thio-$C_1$-$C_4$-alkylene, E represents hydrogen, $C_1$-$C_6$-alkyl, $C_2$-$C_6$-alkenyl, $C_2$-$C_6$-alkynyl, $C_1$-$C_6$-haloalkyl having 1 to 13 fluorine and/or chlorine atoms, $C_2$-$C_6$-haloalkenyl having 1 to 11 fluorine and/or chlorine atoms, $C_1$-$C_6$-haloalkylsulfonyl having 1 to 13 fluorine and/or chlorine atoms, $C_3$-$C_6$-cycloalkyl, di($C_1$-$C_6$-alkyl)aminocarbonyl or di($C_1$-$C_6$-alkyl)aminosulfonyl, W$^1$ represents fluorine, chlorine, bromine, $C_1$-$C_4$-alkyl, $C_1$-$C_4$-alkoxy, $C_1$-$C_4$-haloalkyl having 1 to 9 fluorine and/or chlorine atoms, $C_1$-$C_4$-haloalkoxy having 1 to 9 fluorine and/or chlorine atoms, $C_1$-$C_4$-alkyl-carbonyl, $C_1$-$C_4$-alkoxycarbonyl, —SO$_2$NR$^7$R$^8$ or —S(O)$_o$R$^6$, n represents 0, 1, 2 or 3, o represents 0, 1 or 2, R$^6$ represents $C_1$-$C_6$-alkyl or represents methyl or ethyl, each of which is substituted by 1 to 5 fluorine and/or chlorine atoms, R$^7$ and R$^8$ independently of one another represent hydrogen, $C_1$-$C_4$-alkyl, $C_1$-$C_4$-haloalkyl having 1 to 9 fluorine, chlorine and/or bromine atoms, or together represent —(CH$_2$)$_5$—, —(CH$_2$)$_4$—, —(CH$_2$)$_2$—O—(CH$_2$)$_2$—or —(CH$_2$)$_2$—S—(CH$_2$)$_2$—.

4. A process as claimed in claim 1, wherein the aroylpyrrolidinone of the Formula (II) is

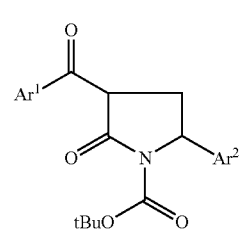
(II)

in which

Ar$^1$ represents the radical

Ar² represents the radical

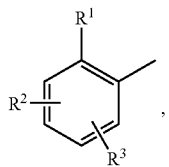

,

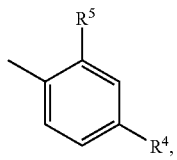

,

R¹ represents fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, trifluoromethyl or trifluoromethoxy, R² and R³ independently of one another represent hydrogen, fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, trifluoromethyl or trifluoromethoxy, R⁴ represents fluorine, chlorine, bromine or one of the groupings below
(l) —X—A
(m) —B—Z—D
(n) —Y—E R⁵ represents hydrogen, fluorine, chlorine, bromine, hydroxyl, methyl, ethyl, methoxy, ethoxy, i-propoxy, methylthio, ethylthio, trifluoromethyl, difluoromethoxy, trifluoromethoxy, trifluoromethylthio or —SO₂CF₃, X represents a direct bond, O (oxygen), S (sulfur), SO₂, carbonyl, —CH₂—, —(CH₂)₂—, —CH═CH— (E or Z), —C≡C—, —CH₂O—, —(CH₂)₂O—, —OCH₂—, —SCH₂—, —S(CH₂)₂—, —OCH₂O— or —O(CH₂)₂O—, A represents phenyl which is optionally mono- or disubstituted by radicals from the list W¹, B represents p-phenylene which is optionally monosubstituted by radicals from the list W¹, Z represents O (oxygen), S (sulfur) or SO₂, D represents hydrogen, methyl, ethyl, n-propyl, i-propyl, n-butyl, i-butyl, s-butyl, t-butyl, 2-propenyl, butenyl, propargyl, butynyl, —CF₃, —CHF₂, —CClF₂, —CF₂CHFCl, —CF₂CH₂F, —CF₂CCl₃, —CH₂CF₃, —CF₂CHFCF₃, —CH₂CF₂H, —CH₂CF₂CF₃, —CF₂CF₂H, —CF₂CHFCF₃, —CO₂Me, —CO₂Et, —SO₂CF₃, —SO₂(CF₂)₃CF₃, —SO₂NMe₂, Y represents a direct bond, O (oxygen), S (sulfur), SO₂, carbonyl, —CH₂—, —(CH₂)₂—, —CH═CH— (E or Z), —C≡C—, —CH₂O—, —(CH₂)₂O—, —OCH₂—, —SCH₂—, —S(CH₂)₂—, —OCH₂O— or —O(CH₂)₂O—, E represents hydrogen, methyl, ethyl, n-propyl, i-propyl, n-butyl, i-butyl, s-butyl, t-butyl, 2-propen-1-yl, butenyl, propargyl, butynyl, —CF₃, —CHF₂, —CClF₂, —CF₂CHFCl, —CF₂CH₂F, —CF₂CCl₃, —CH₂CF₃, —CF₂CHFCF₃, —CH₂CF₂H, —CH₂CF₂CF₃, —CF₂CF₂H, —CF₂CHFCF₃, —SO₂CF₃, —SO₂(CF₂)₃CF₃, cyclohexyl, dimethylaminocarbonyl, —SO₂NMe₂, W¹ represents fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, trifluoromethoxy, difluoromethoxy, —CF₃, —CHF₂, —CClF₂, —CF₂CHFCl, —CF₂CH₂F, —CF₂CCl₃, —CH₂CF₃, —CF₂CHFCF₃, —CH₂CF₂H, —CH₂CF₂CF₃, CF₂CF₂H, —CF₂CHFCF₃, —SCF₃, —SCHF₂, —SO₂CHF₂, —SO₂CF₃, —SO₂NMe₂, —COCH₃ or —SO₂Me₂.

5. A process as claimed in claim 1, wherein the aroylpyrrolidinone is a compound of the Formula (II-a)

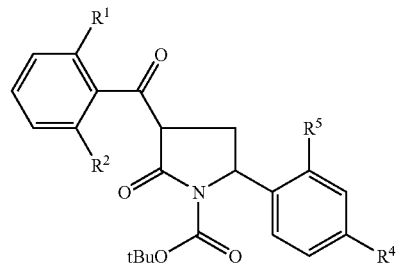

(II-a)

in which
R¹ represents halogen, methyl, methoxy, trifluoromethyl or trifluoromethoxy,
R² represents hydrogen or halogen,
R⁴ represents phenyl which is mono- or disubstituted by radicals from the list W¹ or represents the grouping —Y—E,
R⁵ represents hydrogen or alkoxy and
Y, E, and W¹ are as defined in claim 1.

6. A process as claimed in claim 1, wherein the aroylpyrrolidinone is a compound of the Formula (II-a)

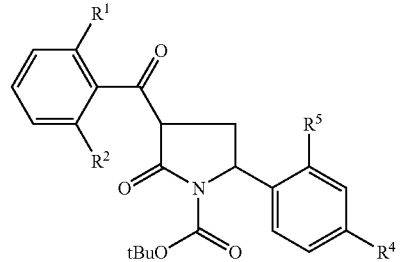

(II-a)

in which
R¹ represents fluorine, chlorine, methyl, methoxy, trifluoromethyl or trifluoromethoxy,
R² represents hydrogen, fluorine or chlorine,
R⁴ represents phenyl which is mono- or disubstituted by radicals from the list W¹ or represents the grouping —Y—E,
R⁵ represents hydrogen or C₁-C₆-alkoxy and
Y, E, and W¹ are as defined in claim 1.

7. A process as claimed in claim 1, wherein the aroylpyrrolidinone is a compound of the Formula (II-a)

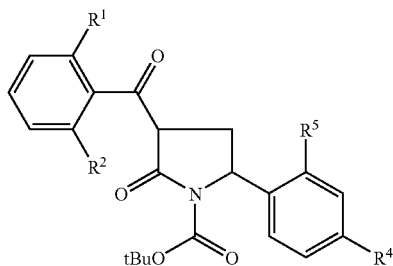

(II-a)

in which
- $R^1$ represents fluorine, chlorine, methyl, methoxy, trifluoromethyl or trifluoromethoxy,
- $R^2$ represents hydrogen, fluorine or chlorine,
- $R^4$ represents phenyl which is mono- or disubstituted by radicals from the list $W^1$ or represents the grouping —Y—E,
- $R^5$ represents hydrogen, methoxy or ethoxy and
- Y, E, and $W^1$ are as defined in claim 1.

8. A process as claimed in claim 1, wherein the aroylpyrrolidinone is a compound of the Formula (II-b)

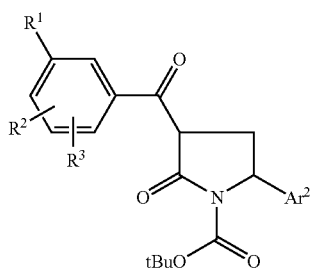

(II-b)

in which
$Ar^2$, $R^1$, $R^2$ and $R^3$ are as defined in claim 1.

9. A process as claimed in claim 1, wherein the aroylpyrrolidinone is a compound of the Formula (II-c)

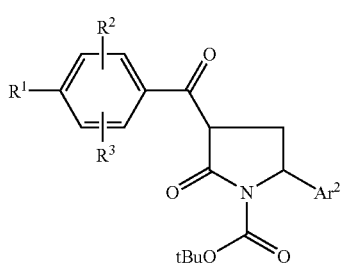

(II-c)

in which
$Ar^2$, $R^1$, $R^2$ and $R^3$ are as defined in claim 1.

10. A process as claimed in claim 1, wherein the aroylpyrrolidinone is a compound of the Formula (II-d)

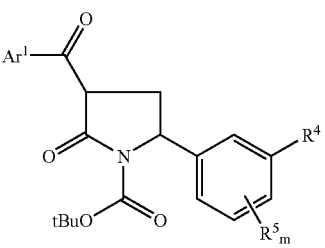

(II-d)

in which
$Ar^1$, $R^4$, $R^5$ and m are as defined in claim 1.

11. A process as claimed in claim 1, wherein the aroylpyrrolidinone is a compound of the Formula (II-e)

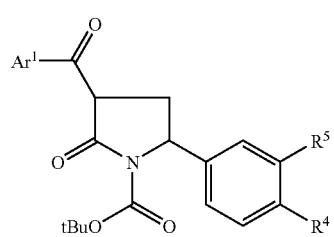

(II-e)

in which
$Ar^1$, $R^4$, $R^5$ and m are as defined in claim 1.

12. A process as claimed in claim 1, wherein the aroylpyrrolidinone is a compound of the Formula (II-f)

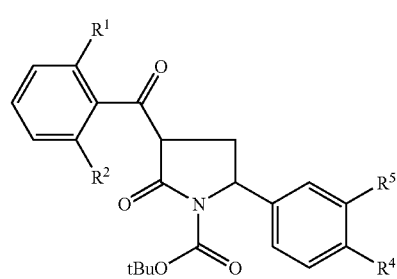

(II-f)

in which
- $R^1$ represents halogen, methyl, methoxy, trifluoromethyl or trifluoromethoxy,
- $R^2$ represents hydrogen or halogen,
- $R^4$ represents phenyl which is mono- or disubstituted by radicals from the list $W^1$ or represents the grouping —Y—E,
- $R^5$ represents hydrogen or alkoxy and
- Y, E, and $W^1$ are as defined in claim 1.

13. A process as claimed in claim 1, wherein the aroylpyrrolidinone is a compound of the Formula (II-g)

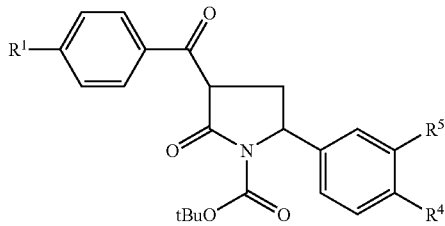

(II-g)

in which
R¹ represents halogen, methyl, methoxy, trifluoromethyl or trifluoromethoxy,
R⁴ represents phenyl which is mono- or disubstituted by radicals from the list W¹ or represents the grouping —Y—E,
R⁵ represents hydrogen or alkoxy and
Y, E, and W¹ are as defined in claim 1.

14. A process as claimed in claim 1, wherein the acid is a protic acid or a strong organic acid or a halocarboxylic acid.

15. A process as claimed in claim 1, wherein the acid is hydrochloric acid, sulfuric acid, hydrofluoric acid, phosphoric acid, p-toluenesulfonic acid, methanesulfonic acid, trifluoroacetic acid or trichloroacetic acid.

16. A process as claimed in claim 1, wherein the diluent is an organic acid.

17. A process as claimed in claim 1, wherein the diluent is propionic acid, acetic acid or formic acid.

18. A process as claimed in claim 1, wherein said acid and said diluent comprise a mixture of sulfuric acid, acetic acid and said mixture further comprises water.

19. A process as claimed in claim 1, wherein the reaction is carried out at temperatures between 20° C. and 200° C.

* * * * *